United States Patent [19]
Sulsky

[11] Patent Number: 5,962,440
[45] Date of Patent: Oct. 5, 1999

[54] CYCLIC PHOSPHONATE ESTER INHIBITORS OF MICROSOMAL TRIGLYCERIDE TRANSFER PROTEIN AND METHOD

[75] Inventor: Richard B. Sulsky, West Trenton, N.J.

[73] Assignee: Bristol-Myers Squibb Company, Princeton, N.J.

[21] Appl. No.: 09/175,180

[22] Filed: Oct. 20, 1998

Related U.S. Application Data

[60] Provisional application No. 60/063,347, Oct. 28, 1997.

[51] Int. Cl.[6] .................. A61K 31/675; A61K 31/66; C07F 9/6574; C07F 9/6541
[52] U.S. Cl. ..................... 514/105; 544/157; 546/22; 548/113; 558/83
[58] Field of Search .................. 514/105; 544/157; 546/22; 548/113; 558/83

[56] References Cited

U.S. PATENT DOCUMENTS 4,952,740  8/1990  Juge et al. .

OTHER PUBLICATIONS

Bentrude, W.G. et al. "Conformations of Six–Membered Ring Phosphorus Heterocyclies, I. The Ring Conformation and Phosphorus Configuration of Isomeric Six–Membered Ring Phosphites", J. of the Amer. Chem. Soc. 92:24, Dec. 2, 1970, pp. 7136–7144.

Cairns, M. et al, "Photorearrangements of Benzyl Phosphites Stereochemistry at Phosphorus", Tetrahedron Letters, vol. 30, No. 9, pp. 1025–1028, 1989.

Wetzel, R. et al. "Synthesis of Phosphine Oxides from Phosphorus Esters and Alkyl Halides Using Either Sodium Bis(2–methoxyethoxy)aluminum Hydride or Sodium Aluminum Diethyl Dihydride", J. Org. Chem., vol. 39, No. 11, 1974, pp. 1531–1535.

Yamashita, M. et al, "Nucleophilic Substitution with Phosphide Anions Prepared by an Action of Sodium Dihydridobis(2–methoxyethanolato)aluminate on Phosphorus Compounds", Bull. Chem. Soc. Jpn., 46,219–222 (1983).

Marsi, K.L. et al, "Preparation of cis– and trans–4–teri–Butyl–1–phenylphosphorinane and a Study of Reaction Stereochemistry of Its Derivatives", J. Org. Chem., vol. 42, No. 8, 1977, pp. 1306–1311.

Montchamp, J–L, et al, "Double Arbuzov Reaction of in Situ Generated Bis(trimethylsiloxy)phosphine with Dielectrophiles: Methodology for the Synthesis of Cyclic Phosphinic Acids", J. Org. Chem. 1995, 60, 6076–6081.

Bentrude, W.G. et al, "Conformations of Saturated Phosphorus Heterocycles. IV. $^1$H, $^{13}$C, and $^{31}$P Nuclear Magnetic Resonance Studies of Geometrical Isomers of 2–Z–4–Methyl–and 4–tert–Butyl–1,3,2–dioxaphospholanes", J. of the Amer. Chem. Soc. 98:7, Mar. 31, 1976, pp. 1850–1859.

Bentrude, W.G. et al, "Conformations of Saturated Cyclic Phosphorus Heterocycles, II, 5–tert–Butyl–2–amino–1,3, 2–dioxaphosphorinanes, Apparent Effects of P–N Vicinal Interactions on the Conformational Energy of Amino Groups on Trivalent Phosphorus . . . ", J. of the Amer. Chem. Soc. 95:14, Jul. 11, 1973, pp. 4666–4675.

Bentrude, W.G. et al, "Free–Radical Chemistry of Organophosphorus Compounds. Free–Radical Arbuzov Reaction Stereochemistries and the Question of Available Permutational Modes for Phosphoranyl Radicals", J. of the Amer. Chem. Soc. 99:13, Jun. 22, 1977, pp. 4383–4390.

*Primary Examiner*—Michael G. Ambrose
*Attorney, Agent, or Firm*—Burton Rodney

[57] ABSTRACT

Novel cyclic phosphonate ester inhibitors of MTP are provided which have the structure

I

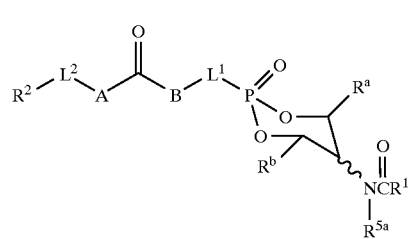

wherein $R^2$, $L^2$, A, B, $L^1$, $R^1$ and $R^{5a}$ are as set out herein. These compounds are useful in lowering serum cholesterol and triglycerides.

15 Claims, No Drawings

CYCLIC PHOSPHONATE ESTER INHIBITORS OF MICROSOMAL TRIGLYCERIDE TRANSFER PROTEIN AND METHOD

This application claims the benefit of U.S. Provisional Application No. 60/063,347; filed Oct. 28, 1997.

FIELD OF THE INVENTION

This invention relates to novel cyclic phosphonate esters which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 3, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., *J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in *The Metabolic Basis of Inherited Disease*, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 82, 1803–6 (1988) and Huang et al., *Am. J. Hum. Genet.* 46, 1141–8 (1990).

Subjects with abetalipoproteinemia are afflicted with numerous maladies. Kane & Havel, vide supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta* 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., *J. Biol. Chem.* 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event. However, there is no direct evidence in the prior art demonstrating that MTP plays a role in lipid metabolism or the assembly of plasma lipoprotein.

Recent reports (Science, Vol. 258, page 999, 1992; D. Sharp et al, Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) which is incorporated herein by reference), reports MTP inhibitors which also block the production of apoB containing lipoproteins in a human hepatic cell line (HepG2 cells). This provides further support for the proposal that an MTP inhibitor would lower apoB containing lipoprotein and lipid levels in . This Canadian patent application discloses a method for identifying the MTP inhibitors

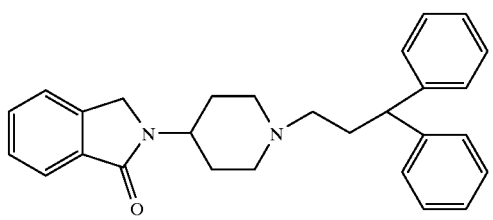

which has the name 2-[1-(3,3-diphenylpropyl)-4-piperidinyl]-2,3-dihydro-3-oxo-1H-isoindole hydrochloride and

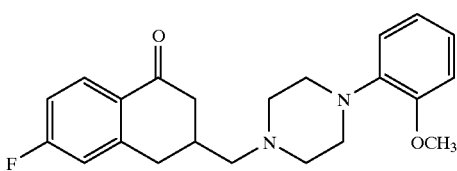

which has the name 1-[3-(6-fluoro-1-tetralanyl)-methyl]-4-O-methoxyphenyl piperazine.

EP 0643057A1 published Mar. 15, 1995, discloses MTP inhibitors of the structure

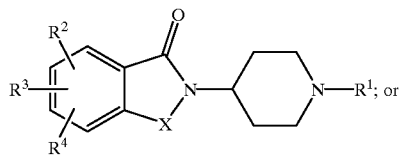

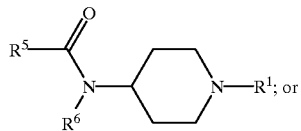

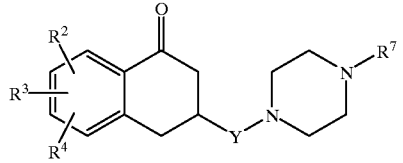

where X is: $CHR^8$, $-\underset{R^9}{CH}-\underset{R^{10}}{CH}-$ or $-\underset{R^9}{C}=\underset{R^{10}}{C}-$;

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)_m-$ or 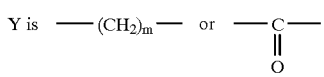

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a group of the structure

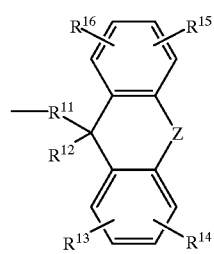

$R^{11}$ is a bond, alkylene, alkenylene or alkynylene of up to 6 carbon atoms, arylene (for example

or mixed arylene-alkylene (for example

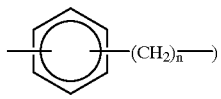

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

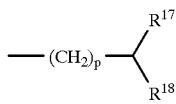

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

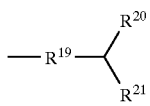

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1$–$C_4$ alkyl or $C_1$–$C_4$ alkenyl;

$R^7$ is alkyl, aryl or arylalkyl wherein alkyl or the alkyl portion is optionally substituted with oxo; and including pharmaceutically acceptable salts and anions thereof or esters thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e) discloses compounds of the structure

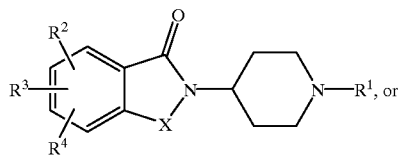

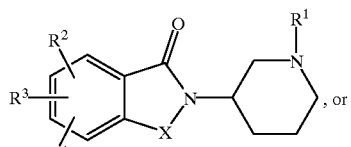

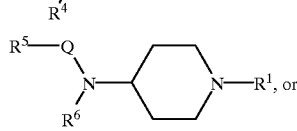

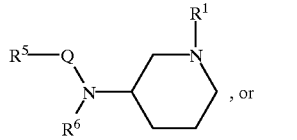

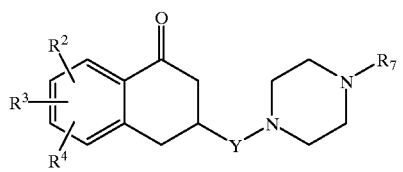

-continued

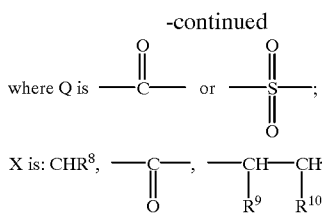

where Q is

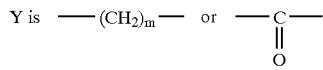

X is: $CHR^8$, $R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is —$(CH_2)_m$— or wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo;

or $R^1$ is a fluorenyl-type group of the structure

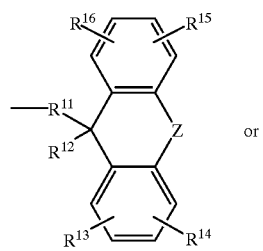
A

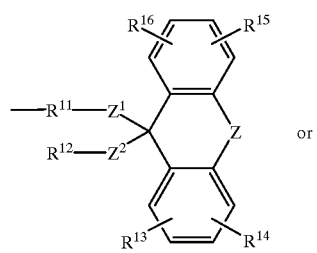
B

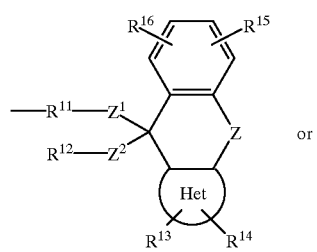
C

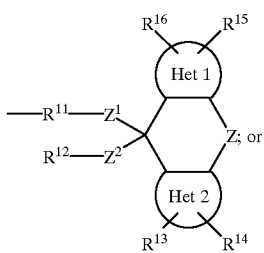
D $R^1$ is an indenyl-type group of the structure

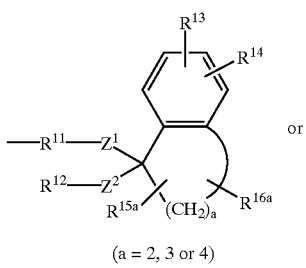
E (a = 2, 3 or 4)

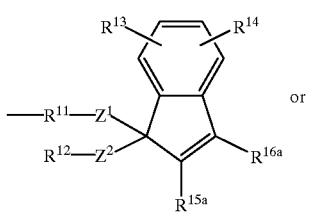
F

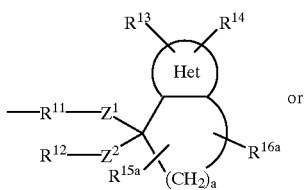
G

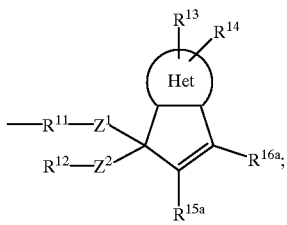
H $Z^1$ and $Z^2$ are the same or different and are independently a bond, O, S,

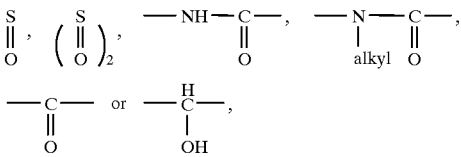

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that
(1) when $R^{12}$ is H, aryloxy, alkoxy or arylalkoxy, then $Z^2$ is

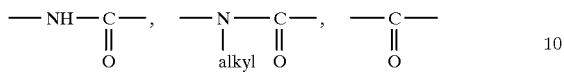

or a bond and
(2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

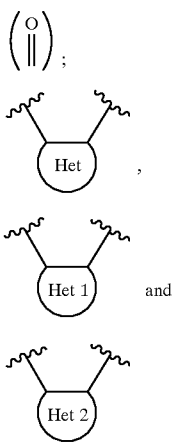

are the same or different and are independently selected from heteroaryl containing 5- or 6-ring members; and N-oxides

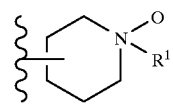

thereof; and pharmaceutically acceptable salts thereof; with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

U.S. Provisional application 60/017,224 filed May 5, 1996, discloses a compound which has the structure

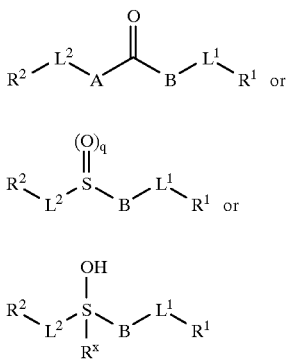 I

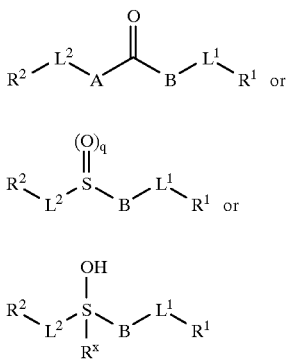 IA

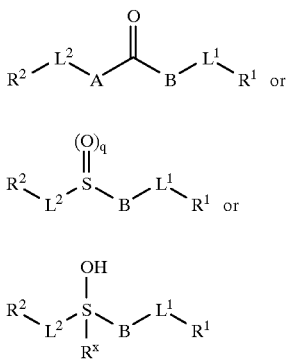 IB including pharmaceutically acceptable salts thereof, N-oxides thereof, wherein q is 0, 1 or 2;

A is
(1) a bond;
(2) —O—; or
(3)

where $R^5$ is H or lower alkyl, or $R^5$ together with $R^2$ forms a carbocyclic or heterocyclic ring system containing 4 to 8 members in the ring;

B is a fluorenyl-type group of the structure

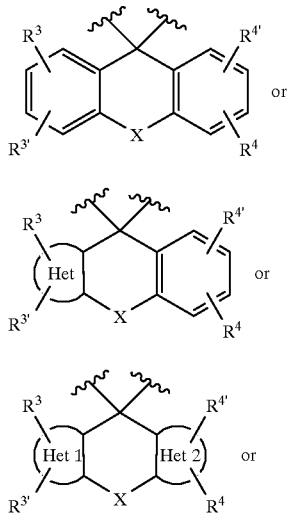

B is an indenyl-type group of the structure

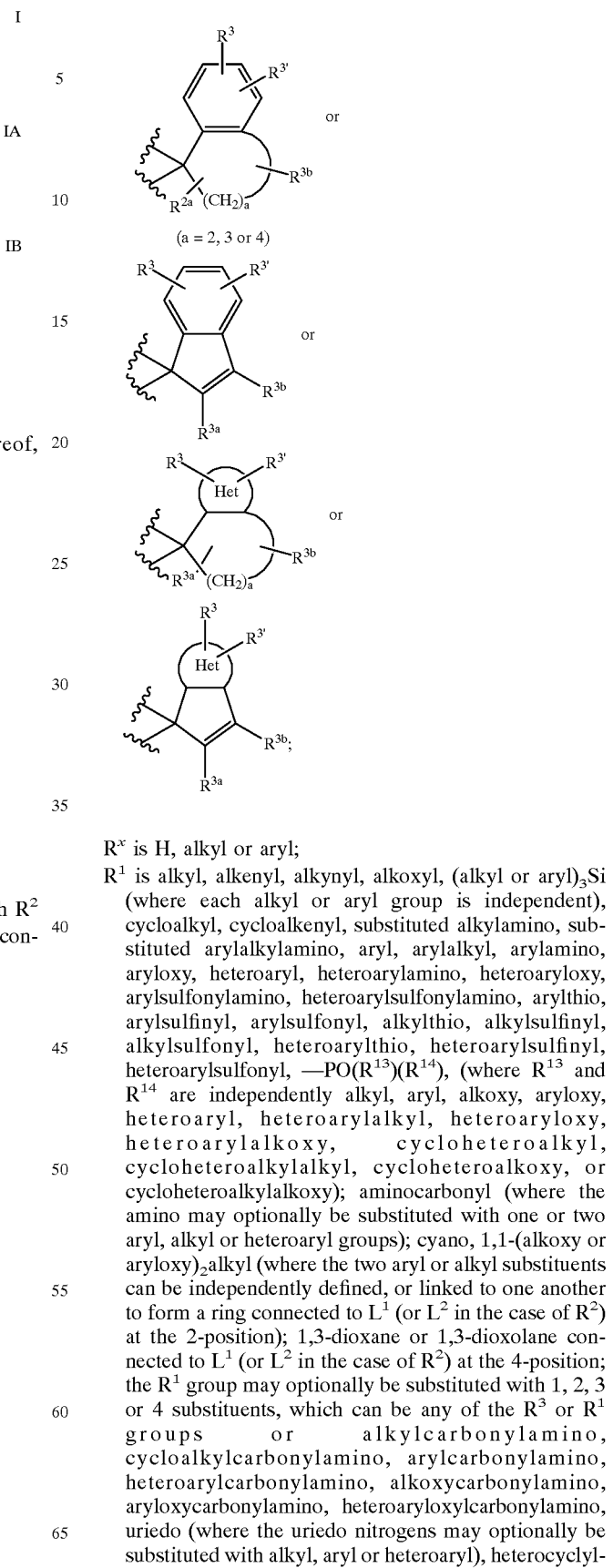

$R^x$ is H, alkyl or aryl;
$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, 1,1-(alkoxy or aryloxy)$_2$alkyl (where the two aryl or alkyl substituents can be independently defined, or linked to one another to form a ring connected to $L^1$ (or $L^2$ in the case of $R^2$) at the 2-position); 1,3-dioxane or 1,3-dioxolane connected to $L^1$ (or $L^2$ in the case of $R^2$) at the 4-position; the $R^1$ group may optionally be substituted with 1, 2, 3 or 4 substituents, which can be any of the $R^3$ or $R^1$ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

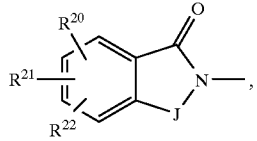

where J is: CHR$^{23}$,

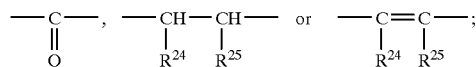

R$^{23}$, R$^{24}$ and R$^{25}$ are independently hydrogen, alkyl, alkenyl, alkynyl, aryl, arylalkyl, heteroaryl, heteroarylalkyl, cycloalkyl, or cycloalkylalkyl;

R$^{20}$, R$^{21}$, R$^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to R$^{1}$, or attached via an alkylene at an open position;

R$^{2}$ is independently any of the groups set out for R$^{1}$, H, polyhaloalkyl, or cycloheteroalkyl, and may be optionally substituted with one to four of any of the groups defined for R$^{3}$ or substituents defined for R$^{1}$;

L$^{1}$ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

L$^{2}$ may be the same or different from L$^{1}$ and may independently be any of the L$^{1}$ groups set out above or a singe bond;

R$^{3}$, R$^{3'}$, R$^{4}$ and R$^{4'}$ may be the same or different and are independently selected from H, halogen, CF$_{3}$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R$^{3a}$ and R$^{3b}$ are the same or different and are independently any of the R$^{3}$ groups except hydroxy, nitro, amino or thio;

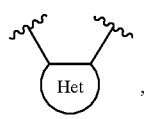

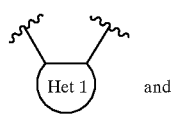

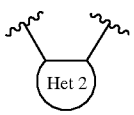

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

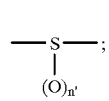 (1)

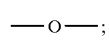 (2)

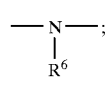 (3)

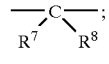 (4)

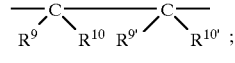 (5)

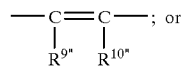 (6)

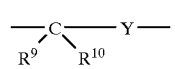 (7)

wherein
Y is O, N—R$^{6}$ or S;
n' is 0, 1 or 2;
R$^{6}$ is H, lower alkyl, aryl, —C(O)—R$^{11}$ or —C(O)—O—R$^{11}$;
R$^{7}$ and R$^{8}$ are the same or different and are independently H, alkyl, aryl, halogen, —O—R$^{12}$, or
R$^{7}$ and R$^{8}$ together can be oxygen to form a ketone;
R$^{9}$, R$^{10}$, R$^{9'}$ and R$^{10'}$ are the same or different and are independently H, lower alkyl, aryl or —O—R$^{11}$;
R$^{9''}$ and R$^{10''}$ are the same or different and are independently H, lower alkyl, aryl, halogen or —O—R$^{11}$;
R$^{11}$ is alky or aryl;
R$^{12}$ is H, alkyl or aryl;
with the following provisos for compound of the structure

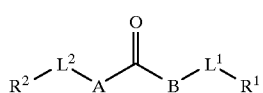

(a) when R$^{1}$ is unsubstituted alkyl or unsubstituted arylalkyl, L$^{1}$ cannot contain amino;
(b) when R$^{1}$ is alkyl, L$^{1}$ cannot contain amino and oxo in adjacent positions (to form an amido group);

(c) when R²L²A— is H₂N—, R¹L¹ cannot contain amino;

(d) when R¹ is cyano, L¹ must have more than 2 carbons;

(e) R¹L¹ must contain at least 3 carbons;

with respect to compounds of formulas I, IA and IB, where R¹ is cycloheteroalkyl, R¹ is exclusive of 1-piperidinyl, 1-pyrrolidinyl, 1-azetidinyl or 1-(2-oxo-pyrrolidinyl);

with respect to the sulfur containing compounds and alcohols, R²L² cannot have an O or N atom directly attached to $S=(O)_q$ or $CR^x(OH)$, and for IA, R²L² cannot be H.

SUMMARY OF THE INVENTION

In accordance with the present invention, novel compounds are provided which are inhibitors of MTP and have the structure

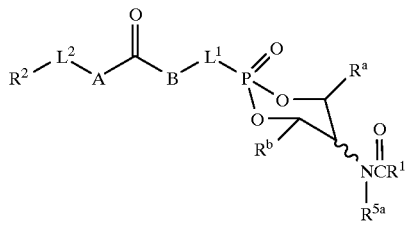

I including pharmaceutically acceptable salts thereof, and stereoisomers and diasteromers thereof wherein A is
(1) a bond;
(2) —O—; or
(3)

where R⁵ is H or lower alkyl or R⁵ together with R² forms a carbocyclic or heterocyclic ring system containing 4 to 8 members in the ring.

B is a fluorenyl-type group of the structure:

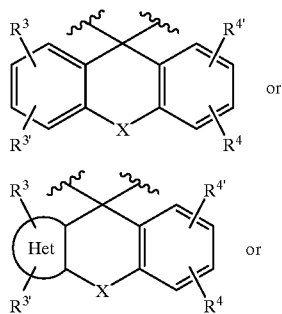

or

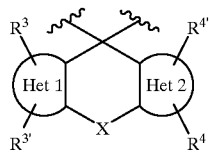

(the above B is also referred to as a fluorenyl-type ring of moiety); or

B is an indenyl-type group of the structure

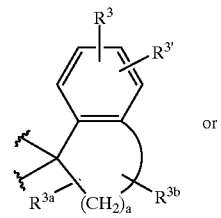

or (a = 2, 3 or 4)

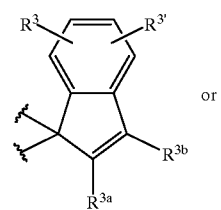

or

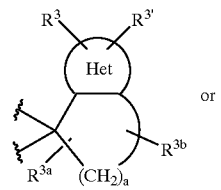

or

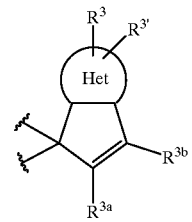

(the above B is also referred to as an indenyl-type ring or moiety);

$R^a$ and $R^b$ may be the same or different and can be hydrogen, alkyl, aryl, arylalkyl or heteroaryl (linked to the ring via a carbon atom);

$R^{5a}$ is H, lower alkyl or aryl;

R¹ is independently alkyl, alkenyl, alkynyl, aryl, alkoxy, aryloxy, arylalkoxy, heteroaryl, heteroarylalkoxy, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl; or $R^1$ and $R^{5a}$ can be joined to form a ring of the structure

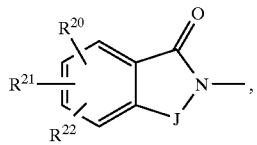

where J is: $CHR^{23}$,

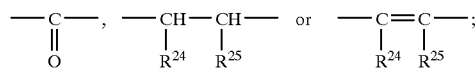

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to $R^1$, or attached via an alkylene chain at an open position.

$R^2$ is hydrogen, alkyl, alkenyl, alkynyl, haloalkyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, cycloheteroalkyl, cycloheteroalkylalkyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkoxyalkyl); or cyano, 1,1-(alkoxyl or aryloxy)$_2$alkyl (where the two aryl or alkyl substituents can be independently defined.

The $R^2$ group may optionally have from one to four substituents, which include any of the $R^1$ substituents, and any of the preferred $R^2$ substituents set out below.

Preferred $R^2$ group when $L^2$ and A are each a single bond include the following: haloalkylamino,(where halo includes $CF_3$), alkylamino, cycloalkylamino, arylamino, heteroarylamino, alkoxyamino, aryloxyamino, heteroaryloxyamino, heterocyclylamino (where the heterocycle is connected to the carbonyl group via a nitrogen or carbon atom).

$L^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

$L^2$ may be the same or different from $L^1$ and may independently be any of the $L^1$ groups set out above or a single bond.

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups;

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

-continued

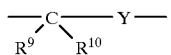

(7)

wherein

Y is O, N—R⁶ or S;

n' is 0, 1 or 2;

$R^6$ is H, lower alkyl, aryl, —C(O)—$R^{11}$ or —C(O)—O—$R^{11}$;

$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9'}$ and $R^{10'}$ are the same or different and are independently H, lower alkyl, aryl or —O—$R^{11}$;

$R^{9''}$ and $R^{10''}$ are the same or different and are independently H, lower alkyl, aryl, halogen or —O—$R^{11}$;

$R^{11}$ is alky or aryl;

$R^{12}$ is H, alkyl or aryl;

with the proviso that when A is a (1) bond, $R^2L^2$ cannot be hydrogen.

The pharmaceutically acceptable salts of the compounds of formula I include alkali metal salts such as lithium, sodium or potassium, alkaline earth metal salts such as calcium or magnesium, as well as zinc or aluminum and other cations such as ammonium, choline, diethanolamine, ethylenediamine, t-butyl-amine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for preventing, inhibiting or treating atherosclerosis, pancreatitis, hyperglycemia or obesity is provided, wherein a compound of formula I, IA or IB as defined hereinbefore is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia, atherosclerosis, hyperglycemia, pancreatitis, obesity, hypertriglyceridemia, Type II diabetes (NIDDM) wherein a compound of formula I as defined hereinbefore is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e. g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents which may be any of the $R^3$ groups, or the $R^1$ substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl and cyclododecyl, cyclohexenyl,

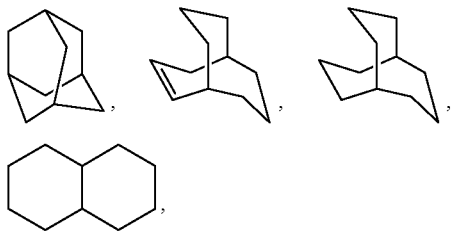

any of which groups may be optionally substituted with 1 to 4 substituents which may be any of the $R^3$ groups, or the $R^1$ substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl or any of the $R^3$ groups, or the $R^1$ substituents set out herein.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the $R^3$ groups, or the $R^1$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^3$ groups, or the $R^1$ substituents set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Suitable alkylene, alkenylene or alkynylene groups or $(CH_2)_m$, $(CH_2)_n$ or $(CH_2)_p$ (which may include alkylene, alkenylene or alkynylene groups) as defined herein, may optionally include 1, 2, or 3 substituents which include any of the $R^3$ groups, or the $R^1$ substituents set out herein.

Examples of alkylene, alkenylene and alkynylene include

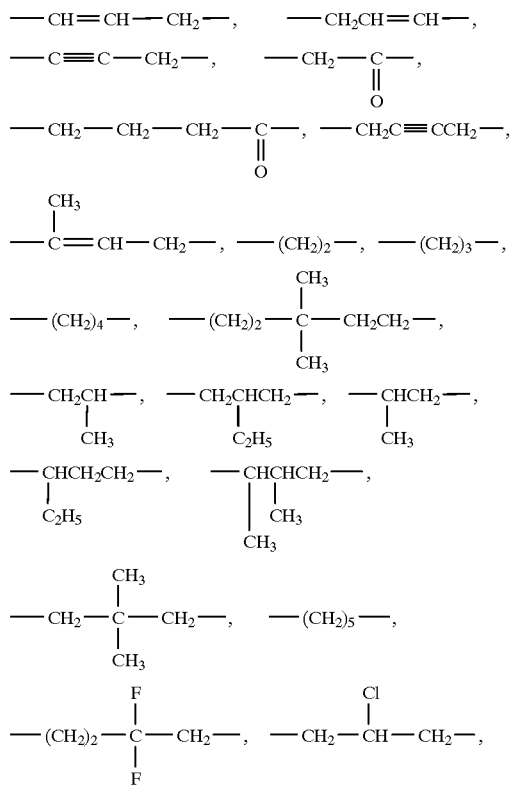

-continued

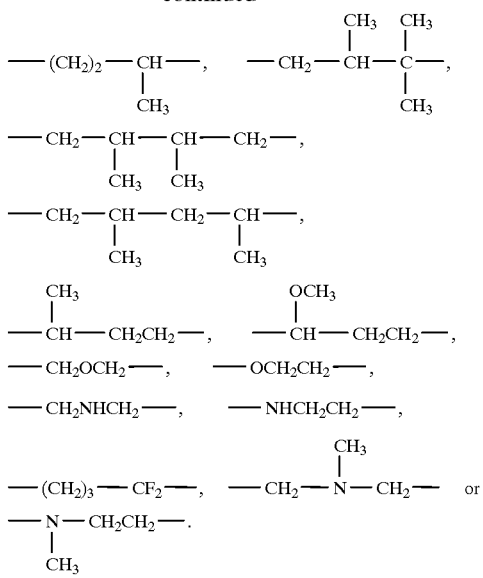

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "heterocyclyl" as used herein refers to "cycloheteroalkyl" groups and "heteroaryl" groups as defined herein.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

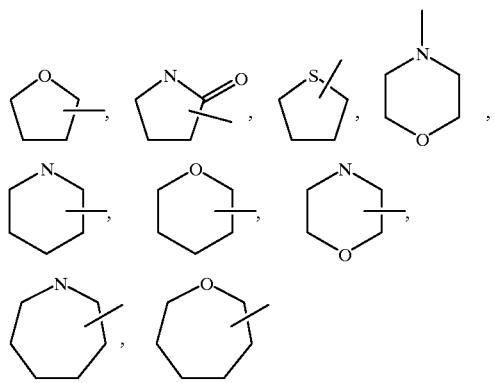

and the like. The above groups may include 1 to 4 substituents such as alkyl, halo, oxo and/or any of of the $R^3$ groups, or the $R^1$ substituents set out herein. In addition, any of the above rings can be fused to a cycloalkyl, aryl, heteroaryl or cycloheteroalkyl ring.

The term "cycloheteroalkoxy" as used herein alone or as part of another group refers to a 4-, 5-, 6- or 7-membered saturated or partially saturated ring which includes at least one oxygen atom in the ring and at least 1 or 2 other hetero atoms in the ring such as nitrogen, oxygen and/or sulfur, linked through a carbon or heteroatom, where possible, optionally via the linker $(CH_2)_p$, such as

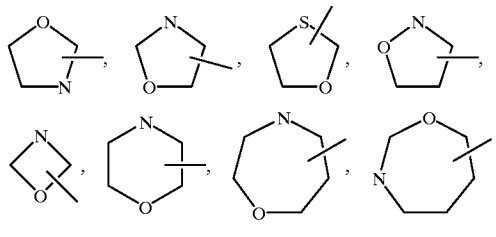

and the like. The above groups may include 1 to 4 substituents such as alkyl, halo, oxo and/or any of of the $R^3$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, such as

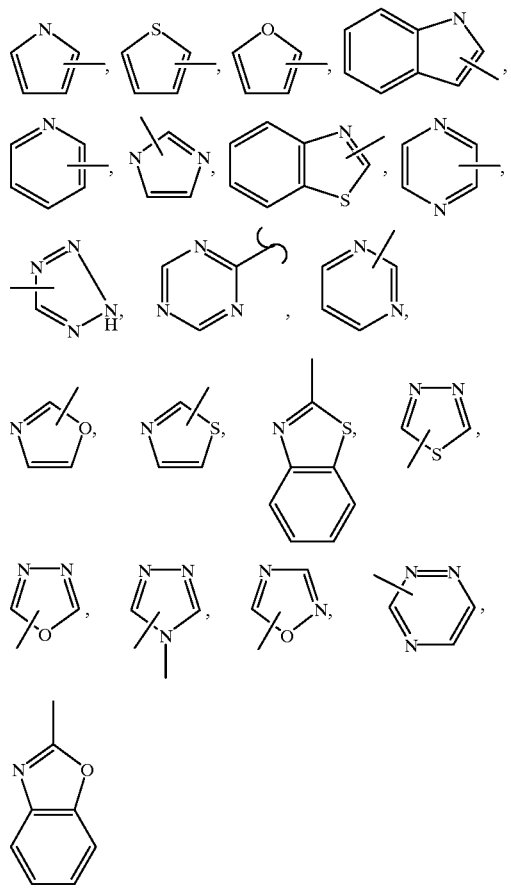

and the like.

Ar may be either aryl or heteroaryl as defined above.

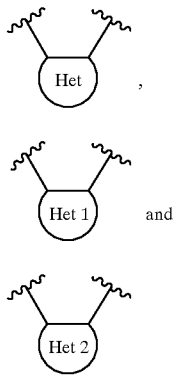

are the same or different, as defined hereinbefore, and are attached to the central ring of the indenyl or fluorenyl type group at adjacent positions (that is, ortho or 1,2-positions). Examples of such groups include

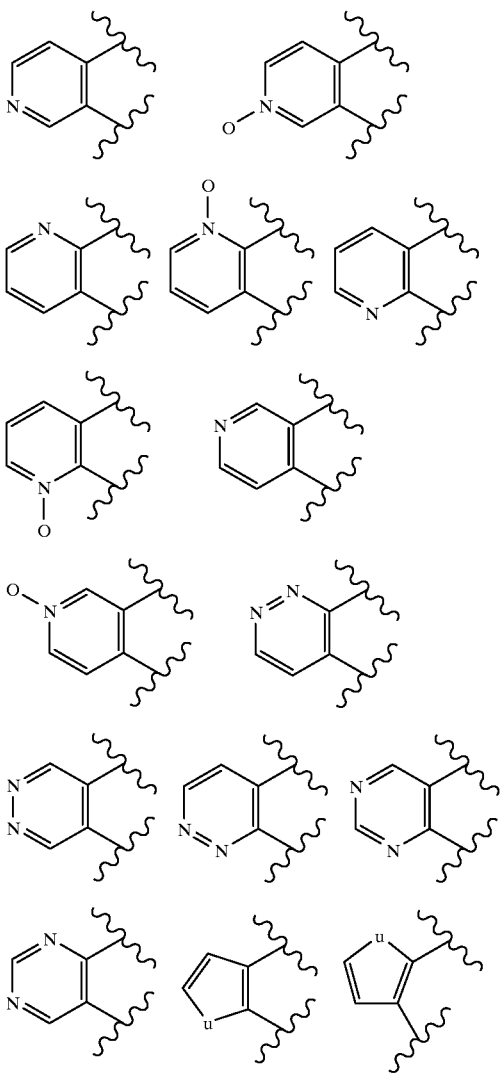

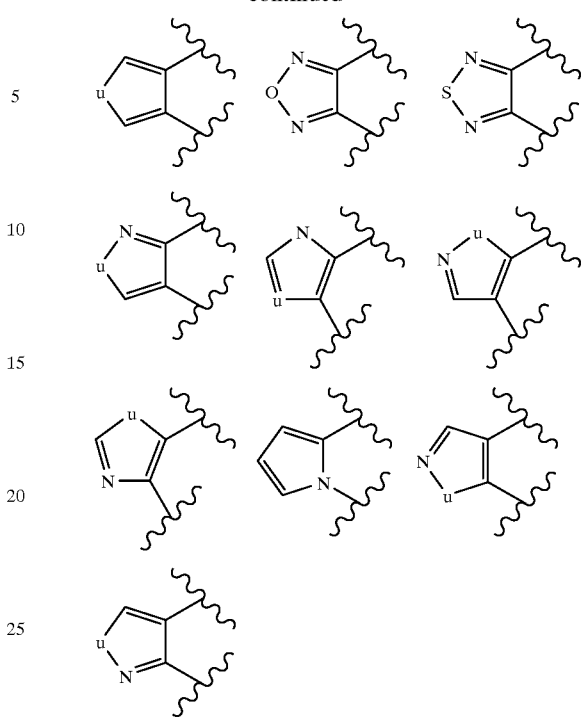

wherein
u is selected from O, S, and $NR^{7a}$;
$R^{7a}$ is H, lower alkyl, aryl, —C(O)$R^{7b}$, —C(O)O$R^{7b}$;
$R^7b$ is alkyl or aryl.

The heteroaryl groups including the above groups may optionally include 1 to 4 substituents such as any of the $R^3$ groups, or the $R^1$ substituents set out herein. In addition, any of the above rings can be fused to a cycloalkyl, aryl, heteroaryl or cycloheteroalkyl ring.

The term cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroaryl-alkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

Preferred are compounds of formula I wherein
A is NH,
B is

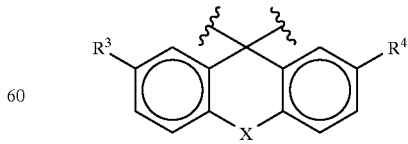

X is a bond, oxygen or sulfur; $R^3$ and $R^4$ are independently H or F.

Preferred $R^2$ groups are alkyl, polyfluoroalkyl (such as 1,1,1-trifluoroethyl), alkenyl, aryl, heteroaryl or heteroarylalkyl, such as 2-pyridylmethyl (preferably substituted with one of the preferred R² substituents above).

It is preferred that L¹ contains 2 to 7 atoms in the linear chain and L² is a bond or lower alkylene.

The preferred L² group is alkylene such as CH₂ or a bond.

The preferred A group is —NH—.

Preferred R¹ groups are as set out in the preferred compounds shown in the following Table.

More preferred are compounds of the invention which have the following structures wherein R¹CO, n and the geometry are as indicated below.

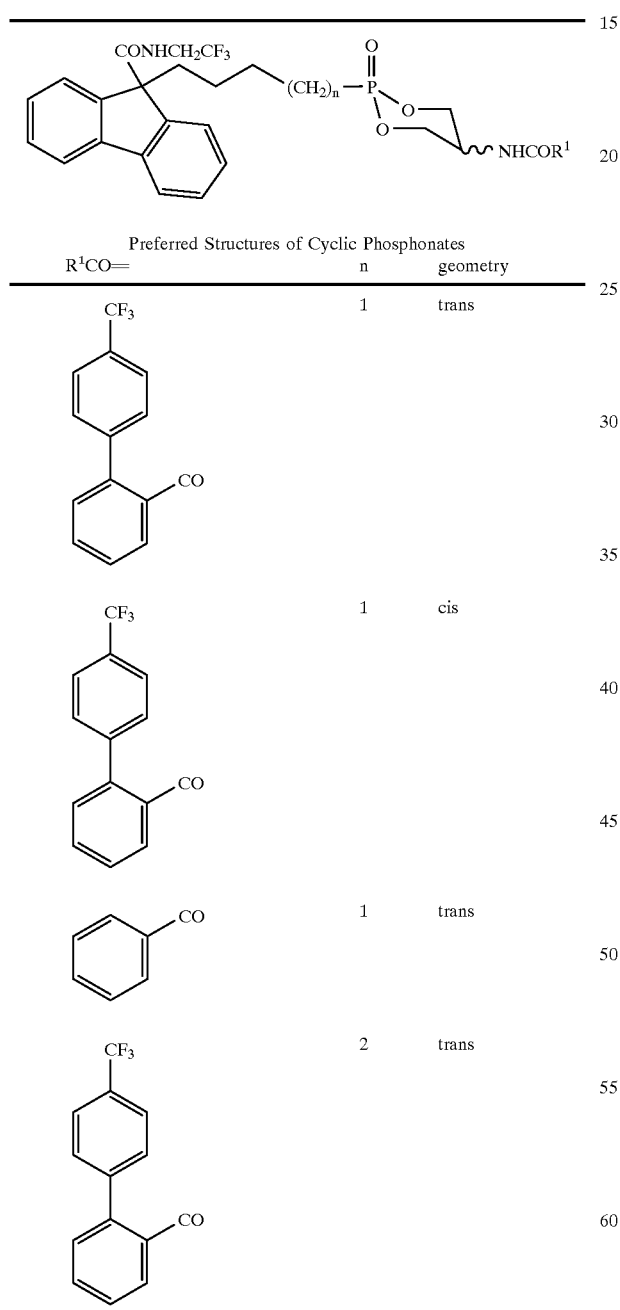

Preferred Structures of Cyclic Phosphonates

| R¹CO= | n | geometry |
|---|---|---|
| CF₃-C₆H₄-C₆H₄-CO | 1 | trans |
| CF₃-C₆H₄-C₆H₄-CO | 1 | cis |
| C₆H₅-CO | 1 | trans |
| CF₃-C₆H₄-C₆H₄-CO | 2 | trans |
| CF₃-C₆H₄-C₆H₄-CO | 2 | cis |
| C₆H₅CH₂-O-CO- | 1 | trans |
| N-benzylpiperidine-2-CO | 1 | trans |
| 2-(2-pyridyl)phenyl-CO | 1 | trans |
| 2-(benzothiazol-2-yl)phenyl-CO | 1 | trans |

The compounds of formula I may be prepared by the exemplary processes described in the following reaction schemes. Exemplary reagents and procedures for these reactions appear hereinafter and in the working Examples.

Methods for preparing starting materials useful in preparing cyclophosphonates in accordance with the present invention, are shown in the folowing reaction schemes.

As seen in Scheme 1A, serinol derivative (2) can be acylated via carbodiimide coupling directly to 3. Alternatively, as seen in Scheme 1B, 2 can be acylated with acid chlorides to tri-acylated 4. Subsequent solvolysis provides diols 3. As seen in Scheme 1C, the diols 3 could also be prepared from bis-O-trimethylsilylated amine 5, acylation with acid chlorides and subsequent methanolysis to provide 3.

It will be appreciated that in the reactions to follow, unless otherwise indicated, the moiety "B" in the starting materials, intermediates and final products is set out as for purposes of illustration only.

It will be appreciated that the "B" moiety in the starting materials, intermediates and final products in all reactions set forth herein, unless indicated to the contrary, may be any of the fluorenyl-type groups

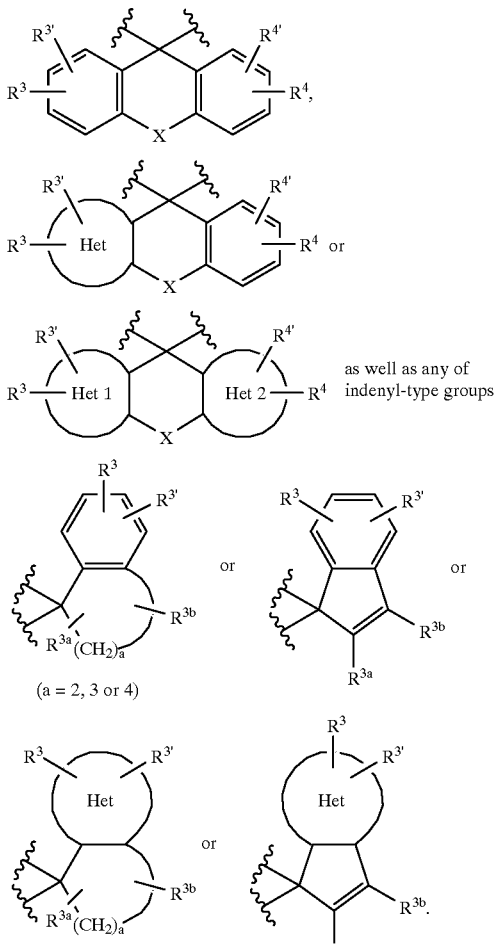

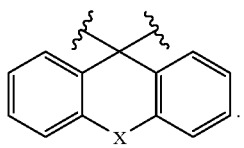

The above B moieties (including all fluorenyl-type groups and all indenyl-type groups) are collectively referred to as "fluorenyl-type" moieties. The use of the first fluorenyl-type group (as set out in the previous paragraph) in the Reaction Schemes is for purposes of illustration only; any of the 3 fluorenyl groups or 4 indenyl groups as set out above may be employed in any of the Reaction Schemes set out herein in place of The compounds of formula I of the invention may be prepared as shown in Reaction Scheme 2.

Scheme 2

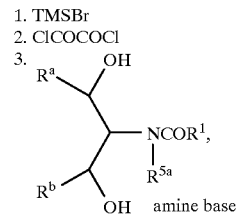

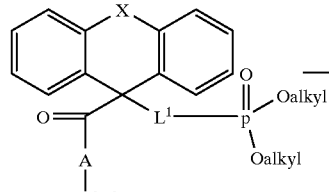

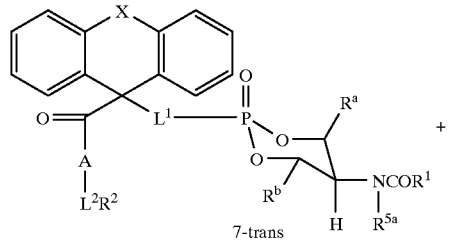

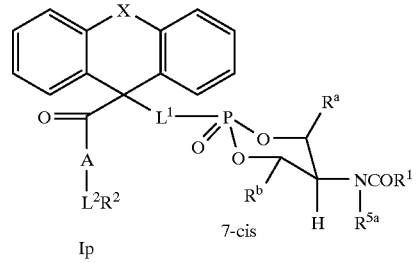

As seen in Scheme 2, dialkyl phosphonate ester Im is treated with bromotrimethylsilane and then is treated with oxalyl chloride and dimethylformamide (employing conventional procedures) to give a diphosphinyl dichloride intermediate which (without purification) is reacted with diol 3 (which may be chiral or achiral) (as formed in Scheme 1A, 1B or 1C) and an amine base such as triethylamine to give a mixture of the 7-trans and 7-cis isomers (Io and Ip, respectively) of the invention. The 7-trans and 7-cis isomers may be separated by conventional chromatographic techniques.

Scheme 3

Preparation of Other Acyl Derivatives From 7-trans Compounds

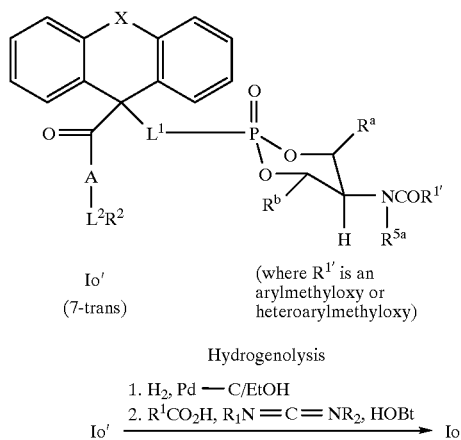

Io'
(7-trans)

(where $R^{1'}$ is an arylmethyloxy or heteroarylmethyloxy)

Hydrogenolysis

1. $H_2$, Pd—C/EtOH
2. $R^1CO_2H$, $R_1N=C=NR_2$, HOBt

Io' $\xrightarrow{}$ Io

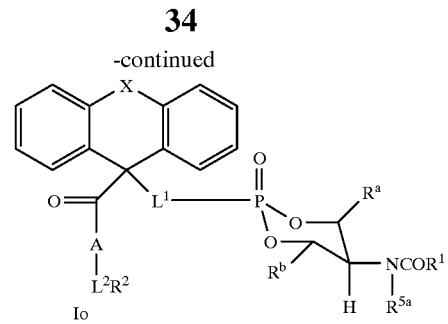

Io
7-trans

As seen in Scheme 3, the 7-trans isomer Io' ($R^{1'}$= $OCH_2C_6H_5$) (and the corresponding 7-cis isomer) may be made to undergo hydrogenolysis to form an amine intermediate which can be reacted with $R^1CO_2H$ to prepare other acyl derivatives in accordance with the invention.

The starting material Im may be prepared according to the following Reaction Schemes 4 and 4A.

Reaction Scheme 4

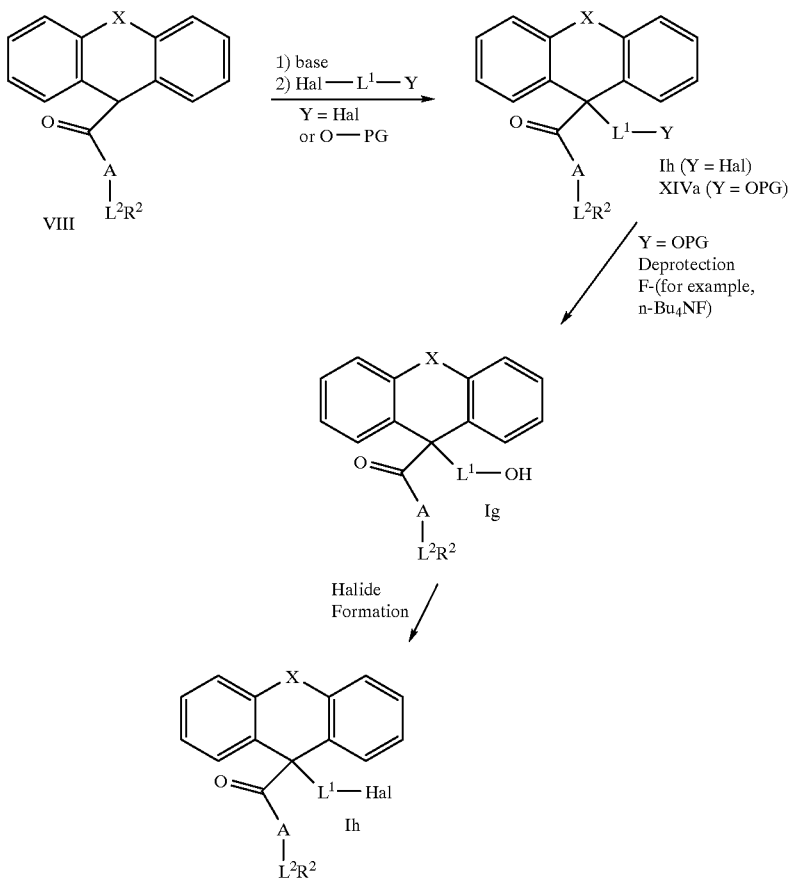

where PG is an oxygen protecting group, such as $t\text{-}Bu(CH_3)_2Si$ or $tBu(Ph)_2Si$—

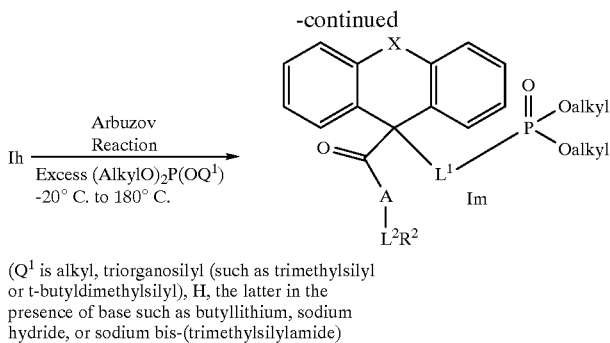

($Q^1$ is alkyl, triorganosilyl (such as trimethylsilyl or t-butyldimethylsilyl), H, the latter in the presence of base such as butyllithium, sodium hydride, or sodium bis-(trimethylsilylamide)

Reaction Scheme 4A (Alternative Method for Making Ih)

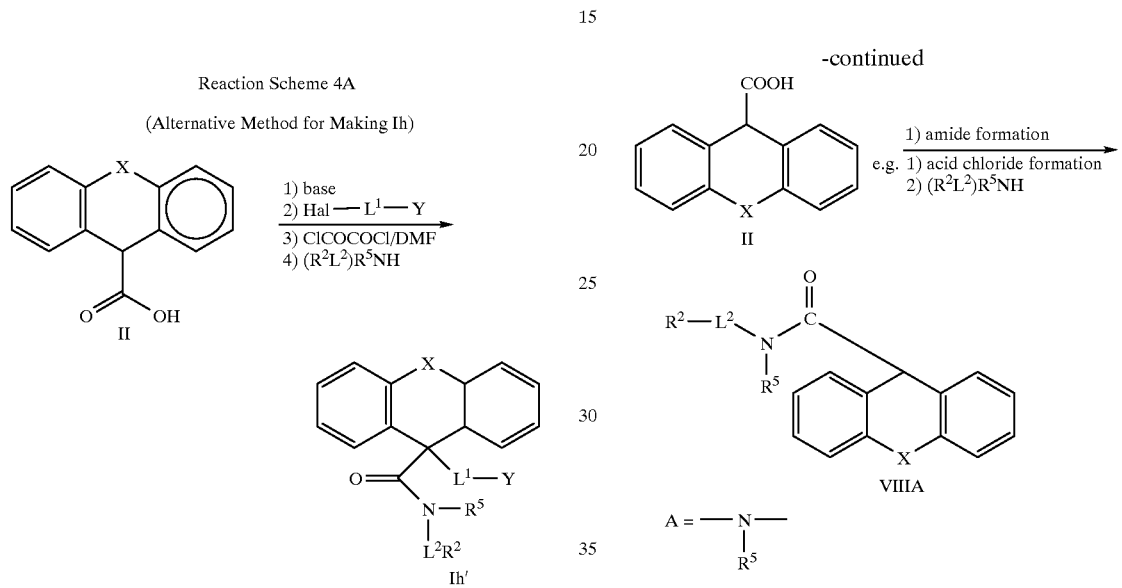

Protected alcohol XIVa can be converted into a wide variety of functional groups through the intermediacy of a halide Ih. For example, the alcohol Ig can be converted to the halide Ih of the invention by either activation through the sulfonate ester (tosyl chloride, or mesyl chloride) and iodide displacement (NaI or KI in acetone or 2-butanone), or by reaction with triphenylphosphine, $I_2$ and imidazole. The halide Ih can undergo an Arbuzov reaction to form phosphonates, phosphinates and phosphine oxides of the invention Im. The Arbuzov reaction can be accomplished with phosphites, phosphinites, and phosphonites (for example, $(alkylO)_3P$ or $(alkylO)_2POSi(alkyl)_3$ or $(alkylO)_2POH$, the latter being in the presence of a base such as butyllithium, sodium hydride or sodium bis (trimethylsilylamide)) at temperatures within the range from about −20° C. to about 180° C.

The starting material VIIIA for compound Im may be prepared as shown in Reaction Scheme 5.

Reaction Scheme 5 (Amides)

Preparation of Compounds of Formula I where A is

As seen in Scheme 5, the amide VIIIA may be formed by treating II with thionyl chloride or oxalyl chloride in an inert organic solvent such as dichloromethane (optionally in the presence of dimethylformamide (DMF)) to form the acid chloride IIA

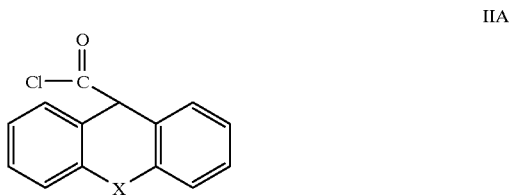

Acid chloride IIA, without separation from the reaction mixture, is treated with amine $(R^2L^2)R^5NH$ at a reduced temperature within the range from about −40° C. to about room temperature, to form the amide VIIIA.

Amide VIIIA may be converted to compounds of formula I employing the procedure set out in Reaction Scheme 4/4A.

In carrying out the above reaction to form amide VIIIA, the amine will be employed in a molar ratio to acid chloride IIA within the range from about 4:1, to about 1:1, optionally in the presence of a tertiary amine base or other acid scavenger.

Alternative formation of amide VIIIA from acid II and $(R^2L^2)R^5NH$ can be carried out via standard literature procedures.

Reaction Scheme 6 (Class Esters)

Preparation of Esters VIIIA (A——O—)

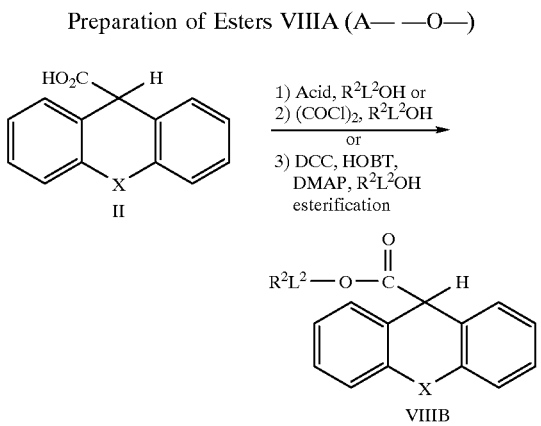

Reaction Scheme 7 (Amides from Isocyanates)

Preparation of Amides VIIIC (A is NH)

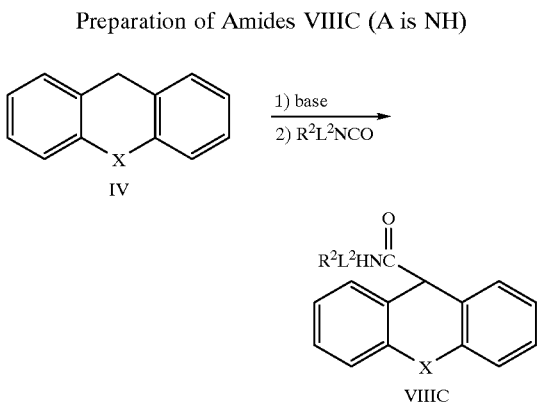

As seen in Reaction Scheme 6, ester compounds of formula VIIIB wherein A=oxygen can be prepared by an acid catalyzed esterification of acid II employing an acid such as $H_2SO_4$ or p-toluene-sulfonic acid in the presence of an alcohol such as allyl alcohol, ethanol or methanol. Alternatively, activation of the acid II to the acid chloride (with oxaly chloride or thionyl chloride) followed by treatment with an alcohol optionally in the presence of a tertiary amine base or other acid scavenger, gives compounds of formula VIIIB.

Various additional methods of activation include mixed anhydride formation $((CF_3COO)_2$ or i-BuOCOCl) or formation of the acylimidazole (carbonyldiimidazole) or with DCC and HOBT in the presence of DMAP (4-dimethylaminopyridine). These activated intermediates readily form esters upon treatment with alcohols.

Compounds of formula VIIIC where A is —NH— (amides) can be prepared by the methods shown in Reaction Scheme 7 from known compound IV. Treatment of compound IV with base, such as n-BuLi, followed by reacting the anion with an isocyanate gives compound VIIIC.

Scheme 8
Alternate Scheme for Compound Im2

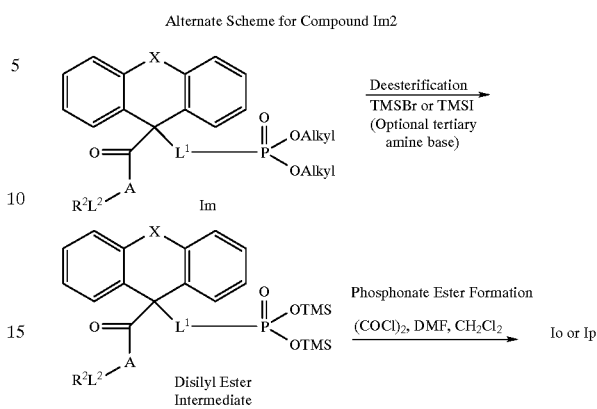

Compounds Im may be modified by the various transformations set out in Reaction Scheme 8.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, employing MTP isolated from one of the following sources:

(1) bovine liver microsomes,
(2) $HepG_2$ cells (human hepatoma cells) or
(3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipemia, hyperlipoproteinemia, hyperlipidemia, pancreatitis, hyperglycemia, atherosclerosis, non-insulin dependent diabetes (Type II diabetes) and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

NOTE: The phrase "flash chromatography" refers to chromatography performed on EM Industries Silica Gel 60 (catalog #9385-9), 230–400 mesh under 10–20 psi of nitrogen pressure.

EXAMPLE 1

(E)-9-[4-[2-Oxo-5-[[[4'-(trifluoromethyl)[1,1'-biphenyl]-2-yl]carbonyl]amino]-1,3,2-dioxaphosphorinan-2-yl]butyl]-N-(2,2,2-trifluoroethyl)-9H-fluorene-9-carboxamide, N-oxide

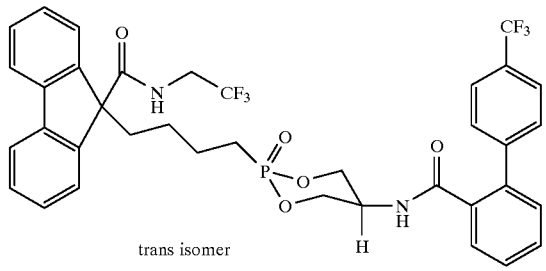

trans isomer

EXAMPLE 2

(Z)-9-[4-[2-Oxo-5-[[[4'-(trifluoromethyl)[1,1'-biphenyl]-2-yl]carbonyl]amino]-1,3,2-dioxaphosphorinan-2-yl]butyl]-N-(2,2,2-trifluoroethyl)-9H-fluorene-9-carboxamide, N-oxide

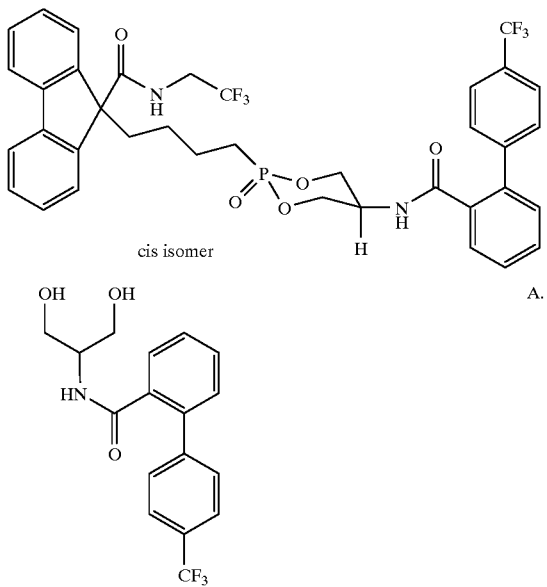

cis isomer

To a stirred solution of 1.33 g (5.00 mmol) of 4'-trifluorophenyl-2-benzoic acid (Aldrich Chemical Co.), 0.455 g (5.00 mmol) of serinol (Aldrich Chemical Co.), 0.750 g (5.0 mmol) of HOBt and 0.5 mL (3.6 mmol) of triethylamine in 10 mL of dichloromethane at room temperature under argon, was added 1.0 g (5.25 mmol) of EDCI, portionwise, over 3 min. After 16 h, the reaction mixture was diluted with ethyl acetate, washed once with saturated sodium bicarbonate solution, once with brine and once with 10% citric acid solution, dried (MgSO$_4$) and evaporated. Purification by flash chromatography on silica gel (5×15 cm column, ethyl acetate) provided title compound as a white solid, mp 146–148° C., 1.23 g, 72% yield.

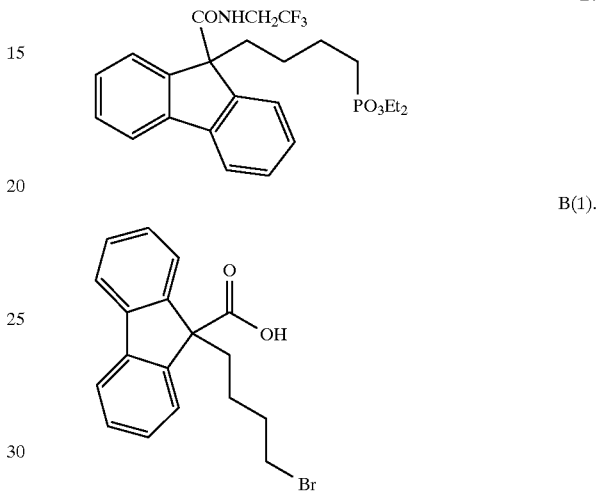

To a solution of 9-fluorenecarboxylic acid (Aldrich) (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

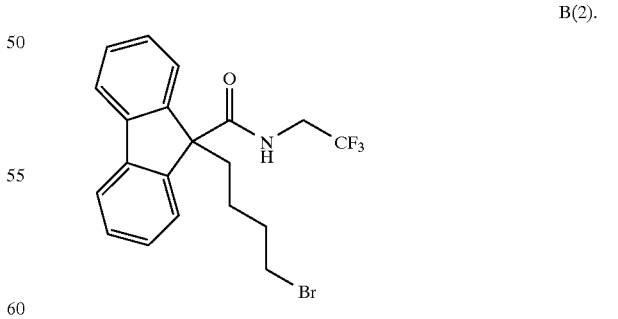

To a solution of Part B(1) acid (60 g, 173 mmol) and DMF (100 μL) in CH$_2$Cl$_2$ (600 mL) under argon at 0° C. was added oxalyl chloride (104 mL, 2.0M in CH$_2$Cl$_2$, 208 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by dropwise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL), saturated NaHCO$_3$ (2×300 mL), and brine (2×300 mL), then dried over MgSO$_4$. Evaporation gave 80 g of a oil which was purified by flash chromatography on silica gel (2.5 kg). The crude product was loaded in a mixture of CH$_2$Cl$_2$ and hexane, and eluted with a step gradient of 10% EtOAc/hexane (4 L) to 15% EtOAc/hexane (2 L) to 20% EtOAc/hexane (4 L). Pure fractions were combined and evaporated to give title compound (52.5 g, 71%) as a white solid (mp 88–92° C.).

B(3).

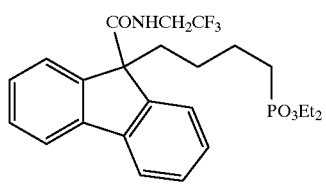

A solution of 2.13 g (5.00 mmol) of Part B(2) compound in 3.5 mL of triethylphosphite under argon was heated to 110° C. for 16 h and then to 180° C. for 4 h. The reaction was cooled and then the volatiles were distilled off at 100° C. at 1 Torr. The residue was purified by flash chromatography (5×15 cm column, EtOAc) to give title compound (1.92 g, 79%) as a waxy yellow solid (mp 87–89° C.).

mp: 87–89° C. MS (FAB) m/e 484 (M+H). Anal. Cald'd for C$_{24}$H$_{29}$NO$_4$PF$_3$+0.13 mol H$_2$O: C, 59.33; H, 6.07; N, 2.88; P, 6.37; F, 11.73. Found: C, 59.09; H, 5.98; N, 2.95; P, 6.51; F, 11.92.

C. (E)-9-[4-[2-Oxo-5-[[[4'-(trifluoromethyl)-[1,1'-biphenyl]-2-yl]carbonyl]amino]-1,3,2-dioxaphosphorinan-2-yl]butyl]-N-(2,2,2-trifluoroethyl)-9H-fluorene-9-carboxamide, N-oxide (Example 1)

D. (Z)-9-[4-[2-Oxo-5-[[[4'-(trifluoromethyl)-[1,1'-biphenyl]-2-yl]carbonyl]amino]-1,3,2-dioxaphosphorinan-2-yl]butyl]-N-(2,2,2-trifluoroethyl)-9H-fluorene-9-carboxamide, N-oxide (Example 2)

To a stirred solution of 500 mg (1.03 mmol) of Part B compound in 10 mL of dichloromethane at room temperature under argon was added 0.45 mL (3.4 mmol) of bromotrimethylsilane. After 1 h, the reaction mixture was evaporated to provide a thick oil. The oil was dissolved in 5 mL of dichloromethane at room temperature under argon and treated with 0.26 mL (3.0 mmol) of oxalyl chloride and 100 µL of DMF. After 2 h, the reaction mixture was evaporated and redissolved in 10 mL of dichloromethane. To this solution at room temperature under argon, was added 340 mg (1.0 mmol) of Part A compound and 0.5 mL (3.6 mmol) of triethylamine. After 14 h, the reaction was diluted with ethyl acetate and washed once with 10% citric acid solution, dried (MgSO$_4$) and evaporated. Purification by flash chromatography on silica gel (5×15 cm column, 1 L 85:15 ethyl acetate/hexanes, then ethyl acetate) provided two fractions.

The less polar fraction was designated Part C (Example 1) compound, white solid, mp 105–107° C., 205 mg, 27% yield.

MICROANALYSIS Calculated for C$_{37}$H$_{33}$F$_6$N$_2$O$_5$P+ 0.55 H$_2$O: C, 60.01; H, 4.64; N, 3.78; F, 15.39; P, 4.18. Found: C, 60.00; H, 4.48; N, 3.64; F, 15.10; P, 3.75. MS (electrospray, +ions) m/e 731.

The more polar fraction was designated Part D (Example 2) compound, white solid, mp 102–104° C., 130 mg, 17%. $^1$H NMR, $^{13}$C NMR, IR and mass spectrometry were consistent for the indicated compound.

MICROANALYSIS Calculated for C$_{37}$H$_{33}$F$_6$N$_2$O$_5$P+ 064 H$_2$O: C, 59.88; H, 4.66; N, 3.77; F, 15.36; P, 4.17. Found: C, 59.88; H, 4.44; N, 3.75; F, 15.08; P, 4.14. MS (electrospray, +ions) m/e 731.

EXAMPLE 3 trans-9-[4-[5-(Benzoylamino)-2-oxo-1,3,2-dioxaphosphorinan-2-yl]butyl]-N-(2,2,2-trifluoroethyl)-9H-fluorene-9-carboxamide

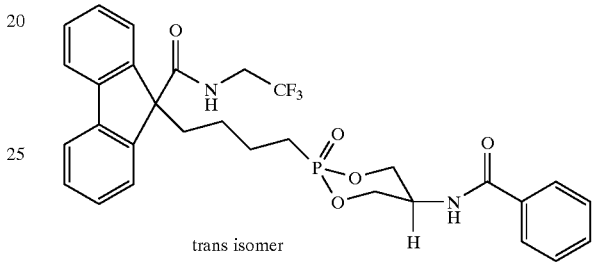

trans isomer

A. N-(1,3-Dibenzoxyloxy-2-propyl)benzamide

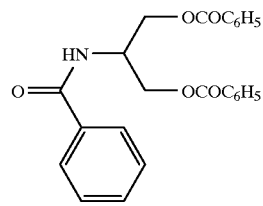

To a stirred slurry of 1.82 g (20.0 mmol) of serinol and 9.2 mL (66 mmol) of triethylamine in 20 mL of dichloromethane at −5° C. under argon, was added dropwise, 7.0 mL (61 mmol) of benzoyl chloride (Aldrich) over 30 min. After 2 h, the reaction was diluted with ethyl acetate and washed three times with 1 M hydrochloric acid, once with brine, twice with saturated sodium bicarbonate solution, dried (MgSO$_4$) and evaporated. The resulting white solid was recrystallized from ethyl acetate/hexane to provide title compound, mp 96–98° C., 5.62 g, 70% yield.

B. N-(1,3-Dihydroxy-2-propyl)benzamide

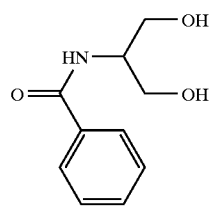

To a stirred solution of 160 mg (4.0 mmol) of 60% sodium hydride in 50 mL of methanol at room temperature under argon, was added 4.03 g (10.0 mmol) of Part A compound. The slurry was heated to reflux where a clear solution forms. After 3 h, the reaction was cooled and 1.5 mL of 4 N hydrogen chloride in dioxane was added. Evaporation and re-evaporation from methanol onto silica gel (5 g) and purification by flash chromatography on silica gel (5×15 cm column, 3:47 methanol/ethyl acetate) gave title compound as white solid, 1.22 g, 62% yield.

C. trans-9-[4-[5-(Benzoylamino)-2-oxo-1,3,2-dioxaphosphorinan-2-yl]butyl]-N-(2,2,2-trifluoroethyl)-9H-fluorene-9-carboxamide To a stirred solution of 699 mg (1.45 mmol) of Example 1 Part B compound in 5 mL of dichloromethane at room temperature under argon was added 0.63 mL (4.8 mmol) of bromotrimethylsilane. After 1 h, the reaction mixture was evaporated to provide a thick oil. The oil was dissolved in 3 mL of dichloromethane at room temperature under argon and treated with 0.26 mL (3.0 mmol) of oxalyl chloride and 50 μL of DMF. After 2 h, the reaction mixture was evaporated and redissolved in 3 mL of dichloromethane. To this solution at room temperature under argon, was added 283 mg (1.45 mmol) of Example 3 Part B compound and 0.6 mL (4.3 mmol) of triethylamine. After 2 h, the reaction was diluted with ethyl acetate and washed once with 10% citric acid solution, dried (MgSO$_4$) and evaporated. Purification by flash chromatography on silica gel (5×15 cm column, ethyl acetate) provided title compound, white solid, mp 166–168° C., 245 mg, 29% yield.

MICROANALYSIS Calculated for $C_{30}H_{30}F_3N_2O_5P+0.5$ $H_2O$: C, 60.50; H, 5.25; N, 4.70; F, 9.57. Found: C, 60.47; H, 5.01; N, 4.62; F, 9.30. MS (electrospray, +ions) m/e 587.

EXAMPLE 4 trans-9-[5-[2-Oxo-5-[[[4'-(trifluoromethyl)[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide

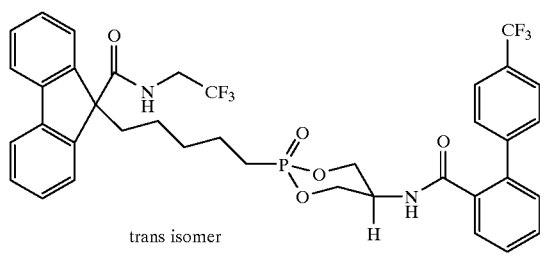

trans isomer

EXAMPLE 5 cis-9-[5-[2-Oxo-5-[[[4'-(trifluoromethyl)[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide

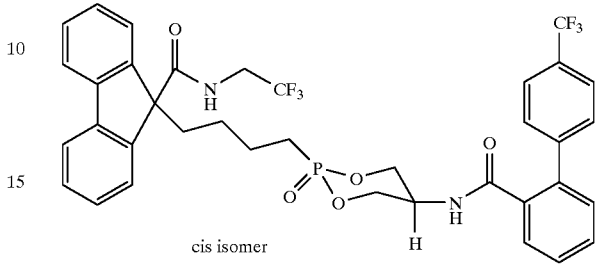

cis isomer

A. 2-Amino-1,3-bis(trimethylsilyloxy)propane

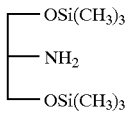

A stirred solution of 1.84 g (20.0 mmol) of serinol in 4.25 mL (20.1 mmol) of hexamethyldisilazane containing 1 drop of bromotrimethylsilane was heated to 180° C. under argon. After 16 h, the reaction mixture was partially cooled and distilled at 0.6 Torr, collecting the fraction with bp 44–47° C. to give title compound as a colorless liquid, 4.05 g, 86%.

B. N-[(1,3-Dihydroxy)-2-propyl]-2-(4-trifluoromethylphenyl)benzamide

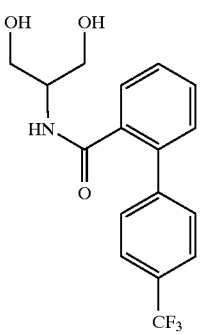

A solution of 4'-trifluoromethyl-2-biphenylcarbonyl chloride [prepared from 4.40 g (16.5 mmol) of the corresponding carboxylic acid] in 10 mL of THF was added dropwise to a solution of 3.88 g (16.5 mmol) of Part A compound and 2.40 mL (17.2 mmol) of triethylamine in 20 mL of THF at 0° C. over 10 min. The resulting slurry was stirred for 1 h, diluted with ether, filtered and the filtrate evaporated. The residual oil was dissolved in 50 mL of methanol and treated with 0.5 mL of 4 M hydrogen chloride in dioxane. After stirring at room temperature for 1 h, the reaction mass was evaporated and the white solid recrystallized from ethyl acetate/hexane to give title compound, mp 146–148° C., 5.08 g, 91% yield.

C.

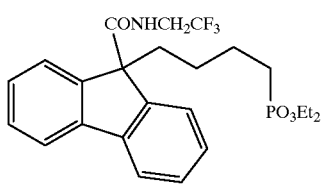

C(1).

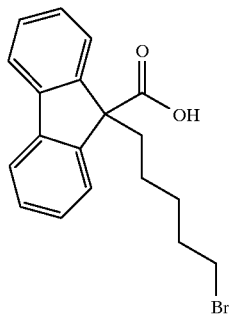

To a solution of 9-fluorenecarboxylic acid (Aldrich) (10 g, 48 mmol) in THF (250 mL) at 0° C. was added dropwise a solution of n-butyllithium (2.5M, 42.2 mL, 106 mmol) in THF. The yellow reaction was stirred at 0° C. for 1 h, then 1,5-dibromobutane (16.8 mL, 124 mmol) was added dropwise over 30 min. The reaction was stirred at 0° C. for 30 min, then the reaction was warmed to RT for 30 h. The reaction was extracted with water (3×150 mL). The combined aqueous layers were extracted with ethyl ether (160 mL). The aqueous layer was made acidic with HCl solution (1N, 100 mL), then extracted with dichloromethane (3×150 mL). The combined organic layers were dried over MgSO$_4$. Evaporation gave title compound as a white solid.

C(2).

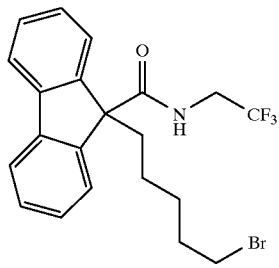

To a solution of all of Part C(1) acid and DMF (20 μL) in CH$_2$Cl$_2$ (120 mL) under argon at 0° C. was added oxalyl chloride (24 mL, 2.0 M in CH$_2$Cl$_2$, 48 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (6.51 g, 48 mmol) in CH$_2$Cl$_2$ (125 mL) at 0° C. under argon was added triethylamine (16 mL, 115 mmol) followed by dropwise addition of a solution of the crude acid chloride in CH$_2$Cl$_2$ (15 mL). The reaction was stirred at 0° C. for 1 h, diluted with CH$_2$Cl$_2$ (120 mL), and washed with water (2×100 mL), 1N HCl (2×100 mL), saturated NaHCO$_3$ (2×100 mL), and brine (2×100 mL), then dried over MgSO$_4$. Evaporation gave 17.6 g of an oil which was purified by flash chromatography on silica gel (500 g). The crude product was loaded in a mixture of CH$_2$Cl$_2$ and hexane, and eluted with a step gradient of 10% EtOAc/hexane (4 L) to 15% EtOAc/hexane (2 L) to 20% EtOAc/hexane (4 L). Pure fractions were combined and evaporated to give title compound (14.7 g, 72%) as a white solid (m.p. 92–96° C.).

C(3).

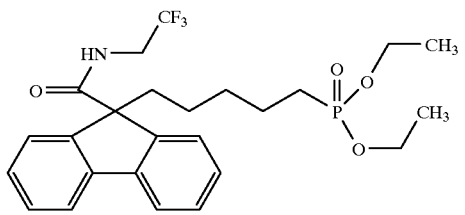

A solution of 2.69 g (6.11 mmol) of Part C(2) compound in 15 mL of freshly distilled triethylphos-phite under argon was heated to 180° C. for 16 h. The reaction was cooled and then the volatiles were distilled off at 100° C. at 1 Torr. The residue was triturated in ether to give title compound (2.25 g, 74%) as a white solid (mp 141–143° C.).

D. trans-9-[5-[2-Oxo-5-[[[4'-(trifluoromethyl)[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide
(Example 4)

E. cis-9-[5-[2-Oxo-5-[[[4'-(trifluoromethyl)[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide
(Example 5)

To a stirred solution of 1.68 g (3.42 mmol) of Part C compound in 10 mL of dichloromethane at room temperature under argon was added 1.35 mL (10.0 mmol) of bromotrimethylsilane. After 14 h, the reaction mixture was evaporated to provide a thick oil. The oil was dissolved in 10 mL of dichloromethane at room temperature under argon and treated with 0.91 mL (10.5 mmol) of oxalyl chloride and 50 μL of DMF. After 2 h, the reaction mixture was evaporated and redissolved in 10 mL of dichloromethane. To this solution at room temperature under argon, was added 1.09 g (3.2 mmol) of Part B compound and 1.0 mL (7.0 mmol) of triethylamine. After 1 h, the reaction was diluted with ethyl acetate and washed once with 10% citric acid solution, dried (MgSO$_4$) and evaporated. Purification by flash chromatography on silica gel (5×20 cm column, 2 L 85:15 ethyl acetate/hexanes, then 2 L 3:97 methanol/ethyl acetate) provided two fractions.

The less polar fraction was designated Part D (Example 4) compound, white solid, mp 165–167° C., 805 mg, 34% yield.

MICROANALYSIS Calculated for C$_{38}$H$_{35}$F$_6$N$_2$O$_5$P+ 0.38 H$_2$O: C, 60.73; H, 4.80; N, 3.73; F, 15.17; P, 4.12. Found: C, 60.73; H, 4.70; N, 3.60; F, 15.33; P, 3.88. MS (electrospray, +ions) m/e 745.

The more polar fraction was designated Part E (Example 5), compound, white foam, mp 110–114° C., 650 mg, 27%.

MICROANALYSIS Calculated for C$_{38}$H$_{35}$F$_6$N$_2$O$_5$P+ 0.38 H$_2$O: C, 60.73; H, 4.80; N, 3.73; P, 4.12. Found: C, 60.74; H, 4.78; N, 3.55; P, 3.84. MS (electrospray, +ions) m/e 745.

EXAMPLE 6 trans-[2-Oxo-2-[4-[9-[[(2,2,2-trifluoroethyl)amino]carbonyl]-9H-fluoren-9-yl]butyl]-1,3,2dioxaphosphorinan-5-yl]carbamic acid, phenylmethyl ester

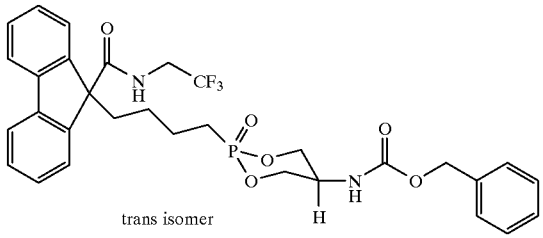

trans isomer

A. N-Benzyloxycarbonyl-1,3-dihydroxy-2-aminopropane

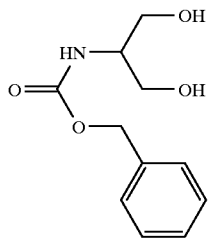

To a stirred slurry of 1.00 g (4.24 mmol) of Example 5 Part A compound and 0.65 mL (4.7 mmol) of triethylamine in 10 mL of THF at 0° C. under argon, was added dropwise, 0.6 mL (4.2 mmol) of benzyloxy carbonyl chloride (Aldrich) over 10 min. The reaction was allowed to warm to room temperature and stirred for 14 h. The reaction mixture was diluted with ether and filtered. The filtrate was evaporated, the residue dissolved in 25 mL of methanol to which 2 drops of 4 N hydrogen chloride in dioxane was added and the solution heated to 40° C. for 30 min. Evaporation and trituration with hexane/ether gave title compound as a white solid, mp 104–106° C., 880 mg, 92% yield.

MS (electrospray, +ions) m/z 226.

B. trans-[2-Oxo-2-[4-[9-[[(2,2,2-trifluoroethyl)amino]carbonyl]-9H-fluoren-9-yl]butyl]-1,3,2-dioxaphosphorinan-5-yl]carbamic acid, phenylmethyl ester To a stirred solution of 1.76 g (3.64 mmol) of Example 1 Part B compound in 5 mL of dichloromethane at room temperature under argon was added 1.65 mL (12.6 mmol) of bromotrimethylsilane. After 1 h, the reaction mixture was evaporated to provide a thick oil. The oil was dissolved in 20 mL of dichloromethane at room temperature under argon and treated with 1.2 mL (13.8 mmol) of oxalyl chloride and 100 µL of DMF. After 2 h, the reaction mixture was evaporated and redissolved in 5 mL of dichloromethane. To this solution at room temperature under argon, was added 820 mg (3.64 mmol) of Part A compound and 1.1 mL (7.9 mmol) of triethylamine. After 2 h, the reaction was diluted with ethyl acetate and washed once with 10% citric acid solution, dried (MgSO$_4$) and evaporated. Purification by flash chromatography on silica gel (5×25 cm column, 85:15 ethyl acetate/hexane) provided title compound, white solid, mp 160–163° C., 535 mg, 23% yield.

MS (electrospray, +ions) m/e 617.

EXAMPLE 7 trans-1-(Phenylmethyl)-N-[2-[4-[9-[[(2,2,2-trifluoroethyl)amino]carbonyl]-9H-fluoren-9-yl]butyl]-1,3,2-dioxaphosphorinan-5-yl]-2-piperdinecarboxamide, hydrochloride

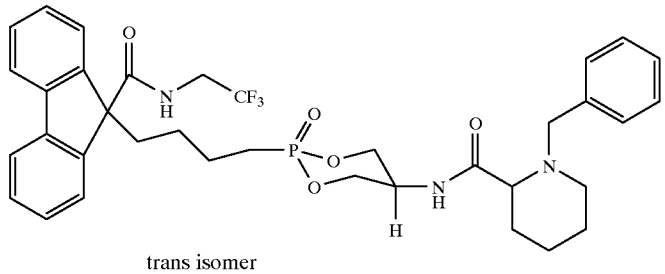

trans isomer

A. N-Benzylpipecolic acid hydrochloride

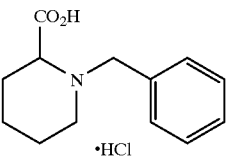

•HCl

A mixture of ethyl pipecolinate hydrochloride (10 g, 52 mmol), benzylbromide (7 mL, 57 mmol) and potassium carbonate (15 g, 114 mmol) in DMF (80 mL) was stirred at room temperature overnight. The solvent was removed in vacuo. The residue was partitioned between dichloromethane (100 mL) and water (50 mL). The aqueous layer was extracted with dichloromethane (2×100 mL), dried over Na$_2$SO$_4$, then evaporated to give a yellow oil. The crude product was chromatographed (500 g silica gel) eluting with a stepgradient of 8%–15% ethyl acetate in hexane. Pure fractions were combined to give title compound (12.3 g, 96%) as a colorless oil.

B. trans-1-(Phenylmethyl)-N-[2-[4-[9-[[(2,2,2-trifluoroethyl)amino]carbonyl]-9H-fluoren-9-yl]butyl]-1,3,2-dioxaphosphorinan-5-yl]-2-piperidinecarboxamide, hydrochloride An argon-purged slurry of 511 mg (0.829 mmol) of Example 6 compound and 100 mg of 10% palladium-on-charcoal in 5 mL of ethanol at room temperature was partially evacuated and subjected to hydrogenation from a filled balloon. After 16 h, the reaction mixture was purged with argon and filtered through a 0.45μ nylon filter. Evaporation and then re-evaporation from dichloromethane gave a white foam. This material was dissolved in 10 mL of dichloromethane and stirred under argon at room temperature while 212 mg (0.83 mmol, HCl salt) of Part A compound, 125 mg (0.83 mmol) of HOBt, 175 mg (0.92 mmol) of EDCI and 175 μL (1.26 mmol) of triethylamine were added. After 6 h, the reaction mixture was quenched with saturated sodium bicarbonate solution and extracted twice with ethyl acetate. The organic extracts were combined, dried (MgSO$_4$) and evaporated. Purification by flash chromatography on silica gel (5×20 cm column, ethyl acetate) provided the free base of title compound. This material was dissolved in dichloromethane, treated with 0.3 mL of 4 M hydrogen chloride in dioxane and evaporated to provide title compound as a white solid, mp 125–128° C., 365 mg, 61% yield.

MICROANALYSIS Calculated for $C_{36}H_{41}F_3N_3O_5P+$HCl+1 dioxane+0.33 H$_2$O: C, 59.01; H, 6.27; N, 5.16; Cl, 4.35; F, 7.00. Found: C, 59.00; H, 6.25; N, 5.11; Cl, 4.14; F, 6.96. MS (electrospray, +ions) m/e 684.

EXAMPLE 8 trans-9-[4-[2-Oxo-5-[[2-(2-pyridinyl)benzoyl]amino]-1,3,2-dioxaphosphorinan-2-yl]butyl]-N-(2,2,2-trifluoroethyl)-9H-fluorene-9-carboxamide, hydrochloride

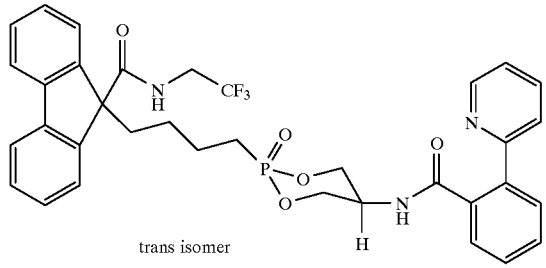

trans isomer

A. 2-(2-Pyridyl)benzoic acid

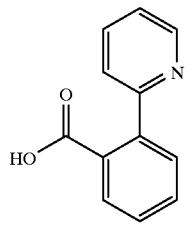

A(1). 2-Methyl-1-(2-pyridyl)benzene

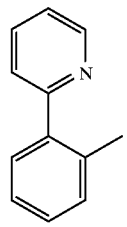

To a degassed solution of 2-bromopyridine (1.9 mL, 20 mmol) in ethylene glycol dimethyl ether (60 mL) under argon, tetrakis(triphenylphosphane) palladium (o) (700 mg, 0.6 mmol) was added. After stirring for 10 min, 2-methylphenyl boronic acid (2.9 g, 22 mmol) was added, followed by sodium bicarbonate solution (5.04 g, 60 mmol in 60 mL water). The mixture was heated to reflux (~85° C.) and stirred overnight. After cooling to room temperature, the solvent was evaporated, the residue was partitioned between water and ether, and the aqueous layer was extracted twice with ether. The combined organic layers were dried (Na$_2$SO$_4$), and the solvent was evaporated to give a black oil. This oil was distilled at <1 Torr at ~95° C. to give title compound (2.75 g, 82% yield) as a clear oil.

A(2).

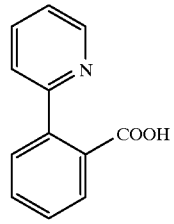

A solution of Part A(1) compound (850 mg, 5.0 mmol) and potassium permanganate (1.9 g, 12.0 mmol) in water (25 mL) was heated to reflux and stirred for 1 hour. The hot reaction mixture was filtered, and the filtrate was evaporated to dryness. The solid residue was dissolved in water (5 mL) and acidified with acetic acid to pH 4–5. The resulting precipitate was isolated by filtration and rinsed with water to give a white solid (800 mg) which was recrystallized from hot ethanol (12 mL) to give title compound as a white solid (453 mg, 45% yield).

B. trans-9-[4-[2-Oxo-5-[[2-(2-pyridinyl)benzoyl]amino]-1,3,2-dioxaphosphorinan-2-yl]butyl]-N-(2,2,2-trifluoroethyl)-9H-fluorene-9-carboxamide, hydrochloride An argon-purged slurry of 505 mg (0.82 mmol) of Example 6 compound and 100 mg of 10% palladium-on-charcoal in 10 mL of methanol at room temperature was partially evacuated and subjected to hydrogenation from a filled balloon. After 4 h, the reaction mixture was purged with argon and filtered through a 0.45μ nylon filter. Evaporation and then re-evaporation from toluene gave a white foam. This material was dissolved in 10 mL of dichloromethane and stirred under argon at room temperature while 169 mg (0.83 mmol) of Part A compound, 162 mg (0.85 mmol) of EDCI and 60 μL (0.43 mmol) of triethylamine were added. After 16 h, the reaction mixture was quenched with saturated sodium bicarbonate solution and extracted twice with ethyl acetate. The organic extracts were combined, dried (Na₂SO₄) and evaporated. Purification by flash chromatography on silica gel (5×15 cm column, 1:24 methanol/ethyl acetate) provided the free base of the title compound. This material was dissolved in dichloromethane, treated with 0.3 mL of 4 M hydrogen chloride in dioxane and evaporated to provide title compound as a white solid, mp 132–136° C., 524 mg, 81% yield.

MICROANALYSIS Calculated for C₃₅H₃₃F₃N₃O₅P+ HCl+dioxane+0.25 H₂O: C, 59.09; H, 5.40; N, 5.30; Cl, 4.47; F, 7.19; P, 3.91. Found: C, 59.12; H, 5.28; N, 5.24; Cl, 4.48; F, 7.37; P, 4.08. MS (electrospray, +ions) m/e 664.

EXAMPLE 9 trans-9-[4-[5-[[2-(2-Benzothiazolyl)benzoyl]amino]-2-oxo-1,3,2-dioxaphosphorinan-2-yl]butyl]-N-(2,2,2-trifluoroethyl)-9H-fluorene-9-carboxamide

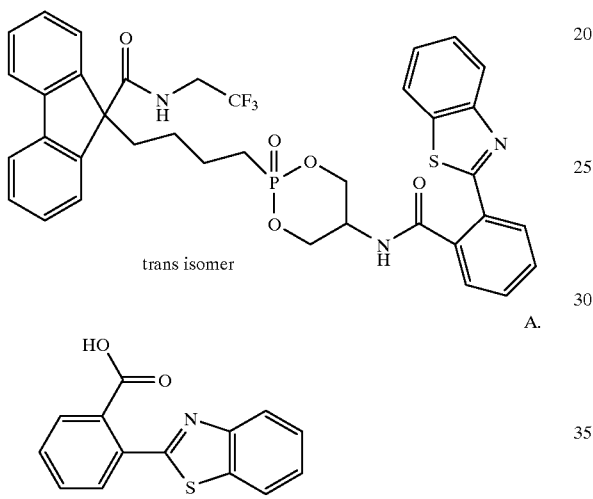

Part A compound is a commercial compound supplied by Maybridge Chemical Company.

B. trans-9-[4-[5-[[2-(2-Benzothiazolyl) benzoyl]amino]-2-oxo-1,3,2-dioxaphosphorinan-2-yl]butyl]-N-(2,2,2-trifluoroethyl)-9H-fluorene-9-carboxamide An argon-purged slurry of 371 mg (0.60 mmol) of Example 6 compound and 90 mg of 10% palladium-on-charcoal in 10 mL of methanol at room temperature was partially evacuated and subjected to hydrogenation from a filled balloon. After 4 h, the reaction mixture was purged with argon and filtered through a 0.45μ nylon filter. Evaporation and then re-evaporation from toluene gave a white foam. This material was dissolved in 5 mL of dichloromethane and stirred under argon at room temperature while 153 mg (0.60 mmol) of Part A compound, 114 mg (0.60 mmol) of EDCI and 42 μL (0.3 mmol) of triethylamine were added. After 16 h, the reaction mixture was quenched with saturated sodium bicarbonate solution and extracted twice with ethyl acetate. The organic extracts were combined, dried (Na₂SO₄) and evaporated. Purification by flash chromatography on silica gel (5×15 cm column, 1:3 hexanes/ethyl acetate) provided title compound as a white solid, mp 117–118° C., 269 mg, 62% yield.

MICROANALYSIS Calculated for C₃₇H₃₃F₃N₃O₅PS: C, 61.75; H, 4.62; N, 5.84; F, 7.92; S, 4.45; P, 4.30. Found: C, 62.02; H, 4.97; N, 5.55; F, 7.64; S, 4.06; P, 4.42. MS (electrospray, +ions) m/e 720.

EXAMPLE 10 trans-9-[4-[5-[[2-(4-Morpholinyl)benzoyl]amino]-2-oxo-1,3,2-dioxaphosphorinan-2-yl]butyl]-N-(2,2,2-trifluoroethyl)-9H-fluorene-9-carboxamide

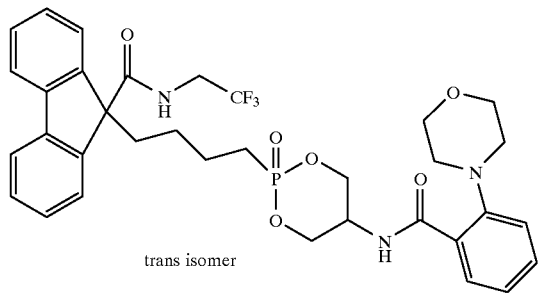

A. 2-(1-Morpholino)benzoic acid

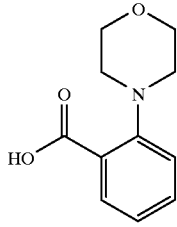

A(1). Methyl 2-(1-morpholino)benzoate

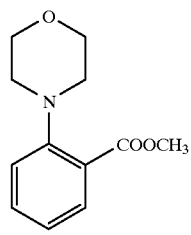

A solution of methyl 2-fluorobenzoate (15.4 g, 100 mmol) in morpholine (44 mL, 500 mmol) was heated at 50° C. for 30 min, and then warmed to 100° C. and stirred for 2 h, then cooled to 50° C. and stirred overnight. The reaction was then heated to reflux for 2.5 h. The excess morpholine was evaporated. The remainder was dissolved in ethyl acetate and washed successively with H₂O (50 mL), saturated NaHCO₃ solution (2×50 mL), H₂O (3×50 mL) and brine (50 mL). Drying (MgSO₄) and evaporation gave a yellow oil. The crude product was dissolved in dichloromethane/ethyl acetate/hexane (4:1:4) and chromatographed (400 g silica gel) eluting with a step gradient of 20% to 35% ethyl acetate in hexane. Pure fractions were combined and evaporated to give title compound (10.5 g, 48%) as an oil which crystallized on standing to a white solid.

A(2). 2-(1-Morpholino)benzoic acid

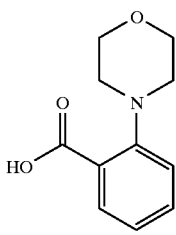

Sodium hydroxide (10 g, 250 mmol) was dissolved in water (75 mL) and added to a solution of Part A(1) compound (10.4 g, 47.1 mmol) in methanol (75 mL). The reaction was stirred at RT for 1 h and the solvent was evaporated. The white residue was dissolved in $H_2O$ (100 mL) and adjusted to pH 1.5 with 1N HCl. The aqueous layer was extracted with chloroform (3×250 mL). The combined organic layers were dried ($Na_2SO_4$) and evaporated to give title compound (9.76 g, 85%) as a white solid (m.p. 156–157° C.).

B. trans-9-[4-[5-[[2-(4-Morpholinyl)benzoyl] amino]-2-oxo-1,3,2-dioxaphosphorinan-2-yl]butyl]-N-(2,2,2-trifluoroethyl)-9H-fluorene-9-carboxamide An argon-purged slurry of 359 mg (0.582 mmol) of Example 6 compound and 100 mg of 10% palladium-on-charcoal in 15 mL of methanol at room temperature was partially evacuated and subjected to hydrogenation from a filled balloon. After 16 h, the reaction mixture was purged with argon and filtered through a 0.45μ nylon filter. Evaporation and then re-evaporation from toluene gave a white foam. This material was dissolved in 5 mL of dichloromethane and stirred under argon at room temperature while 121 mg (0.584 mmol) of Part A compound, 88 mg (0.59 mmol) of HOBt, 122 mg (0.64 mmol) of EDCI and 41 μL (0.3 mmol) of triethylamine were added. After 6 h, the reaction mixture was quenched with saturated sodium bicarbonate solution and extracted twice with ethyl acetate. The organic extracts were combined, dried ($Na_2SO_4$) and evaporated. Purification by flash chromatography on silica gel (5×20 cm column, ethyl acetate) provided title compound as a white solid, mp 108–111° C., 265 mg, 66% yield.

MICROANALYSIS Calculated for $C_{34}H_{37}F_3N_3O_6P+$ 0.15 $H_2O$+0.23 EtOAc: C, 60.38; H, 5.68; N, 6.05; F, 8.21. Found: C, 60.37; H, 5.54; N, 5.93; F, 7.91. MS (electrospray, +ions) m/e 695.

EXAMPLE 11
trans-9-[4-[5-[[2-(2-Benzoxazolyl)benzoyl]amino]-2-oxo-1,3,2-dioxaphosphorinan-2-yl]butyl]-N-(2,2,2-trifluoroethyl)-9H-fluorene-9-carboxamide

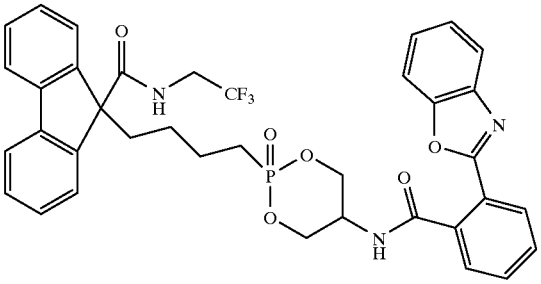

A. 2-(2-Bromophenyl)benzoxazole

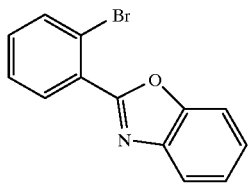

To a stirred slurry of 5.46 g (50.0 mmol) of 2-aminophenol (Aldrich) and 10.05 g (50.0 mmol) of 2-bromobenzoic acid in 100 mL of xylenes under argon at room temperature was added 6.10 g (100 mmol) of boric acid. Using a Dean-Stark trap, the reaction was heated to reflux for 48 h. A total of 3.2 mL of water was separated. The reaction mixture was cooled, diluted with ethyl acetate and filtered. The filtrate was washed once with 3 M hydrochloric acid, once with water and three times with saturated sodium bicarbonate solution. The organic phase was dried (MgSO,) and evaporated. Purification by flash chromatography on silica gel (5×20 cm column, 2:1 dichloromethane/hexane) gave title compound as a light yellow solid, 5.90 g, 43%.

B. 2-(2-Benzoxazolyl)benzoic acid

To a stirred solution of 700 mg (2.55 mmol) of Part A compound in 10 mL of THF under argon at –78° C. was added a solution of t-butyllithium (3.3 mL, 1.7 M, 5.6 mmol) in pentane over the course of 30 min. The reaction mixture was stirred for 1 h and then a dry stream of carbon dioxide gas was passed through the solution for 1 h. The reaction was allowed to warm to room temperature in situ. After 16 h, the mixture was diluted with ether and washed once with 50 mL of 10% sodium hydroxide solution. The aqueous phase was adjusted to pH 3.5 using solid citric acid. The resulting solid was filtered, washed with water and air-dried to give 610 mg of title compound as a pink solid, mp >250° C., 100%.

C. trans-9-[4-[5-[[2-(Benzoxazolyl)benzoyl]amino]-2-oxo-1,3,2-dioxaphosphorinan-2-yl]butyl]-N-(2,2,2-trifluoroethyl)-9H-fluorene-9-carboxamide To a stirred solution of 117 mg (0.24 mmol) of Example 6 compound under argon at room temperature in 3 mL of dichloromethane was added 72 mg (0.30 mmol) of Part B compound, 45 mg (0.3 mmol) of HOBt, 65 mg (0.30 mmol) of EDCI and 20 μL (0.15 mmol) of triethylamine. After 16 h, the reaction mixture was quenched with saturated sodium bicarbonate solution and extracted twice with ethyl acetate. The organic extracts were combined, dried ($Na_2SO_4$) and evaporated. Purification by flash chromatography on silica gel (2.5×15 cm column, 1:3 hexanes/ethyl acetate) provided title compound as a white solid, mp 104–107° C., 38 mg, 20% yield.

MICROANALYSIS Calculated for $C_{37}H_{33}F_3N_3O_6P$+2.3 $H_2O$+0.5 EtOAc: C, 59.36; H, 5.31; N, 5.32; F, 7.22; P, 3.92. Found: C, 59.32; H, 5.24; N, 5.43; F, 7.45; P, 4.20. MS (electrospray, +ions) m/e 704.

Following are examples of additional compounds of the invention which may be prepared employing procedures described hereinbefore and in Examples 1 to 11. Although the following compounds are shown in the form of cis-isomers, in accordance with the invention, the corresponding trans-isomers are covered as well.

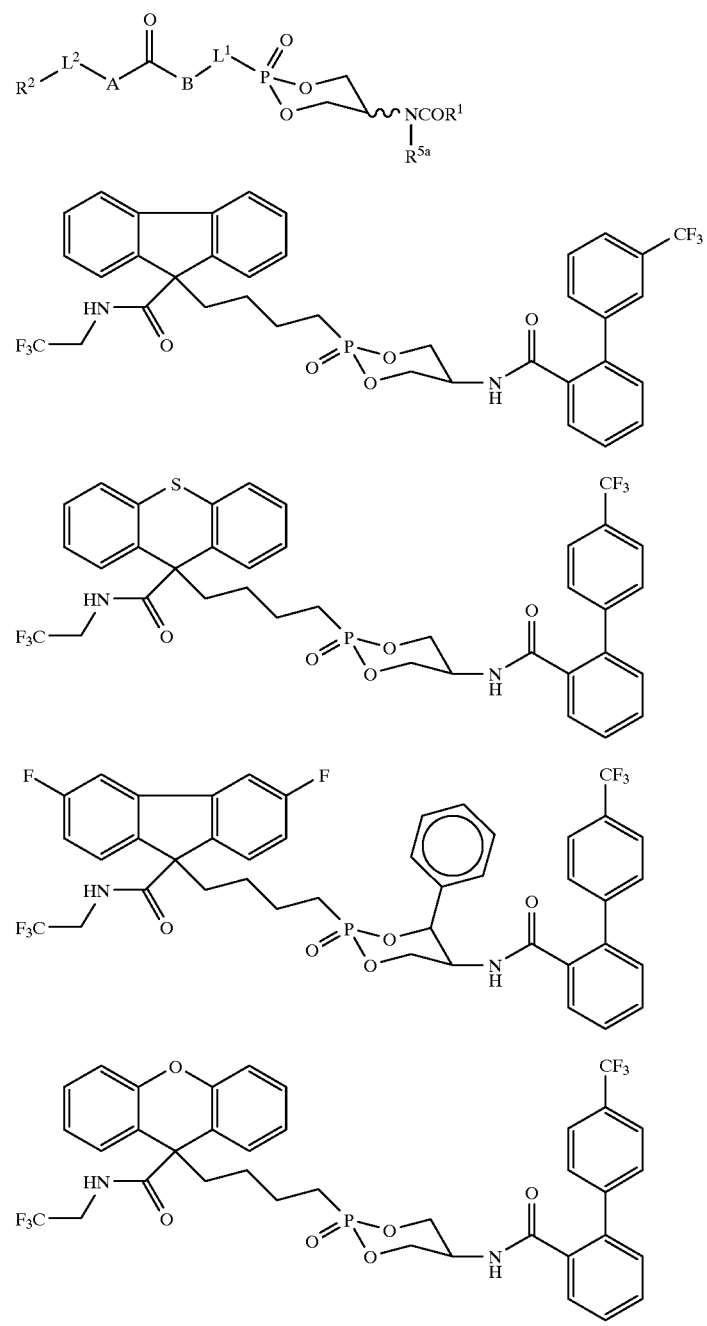

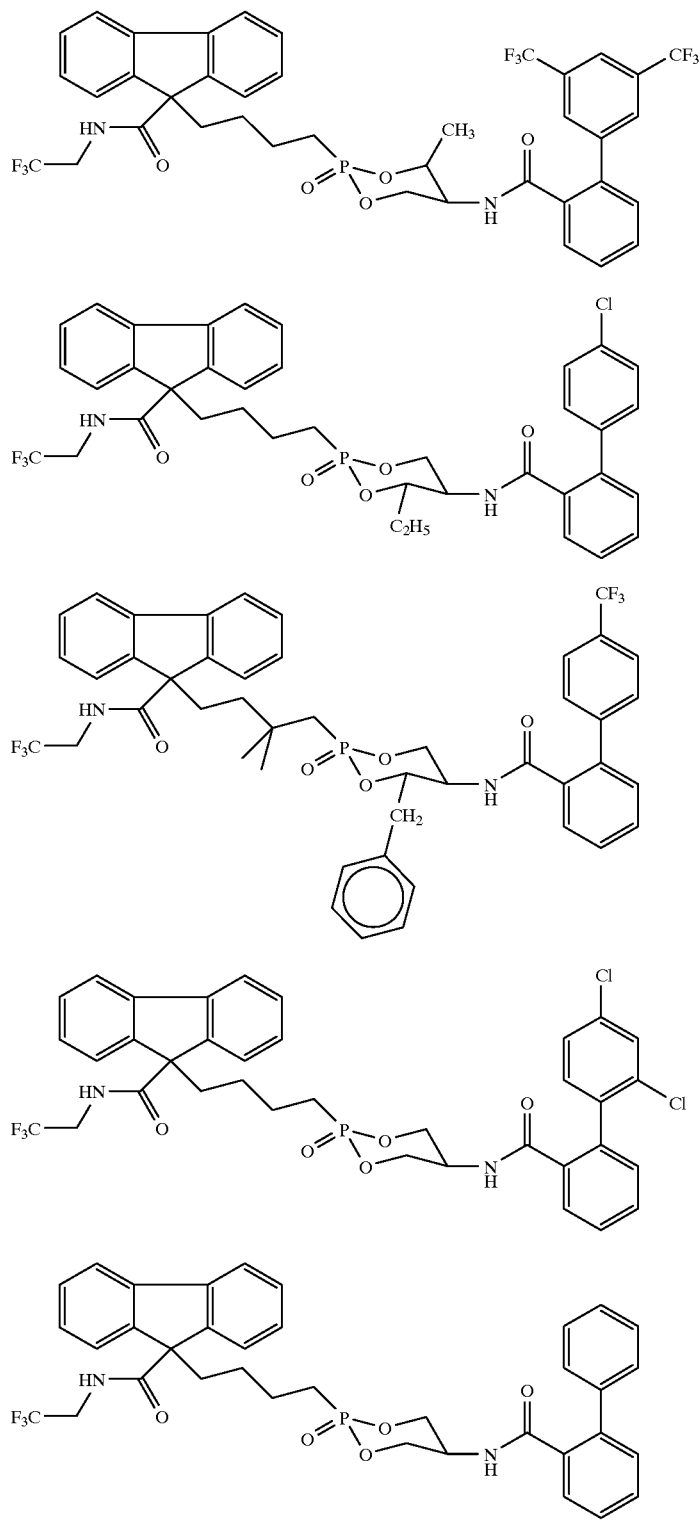

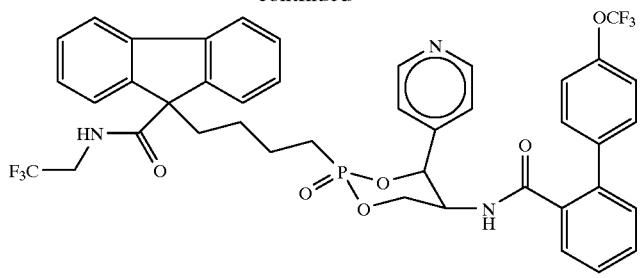
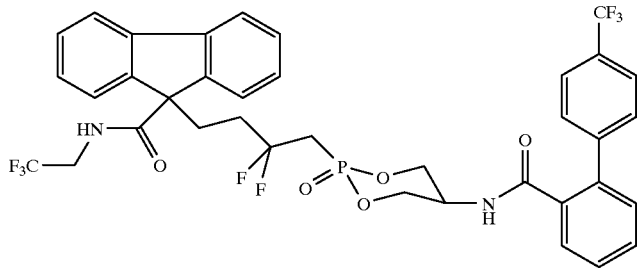
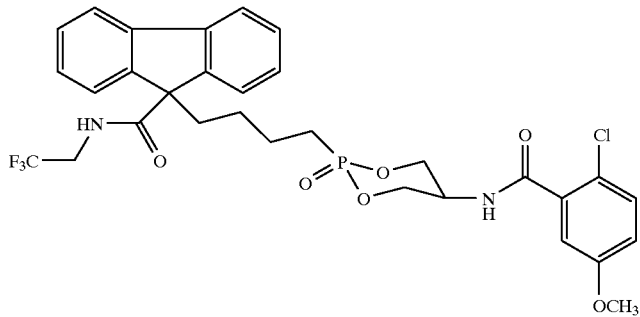
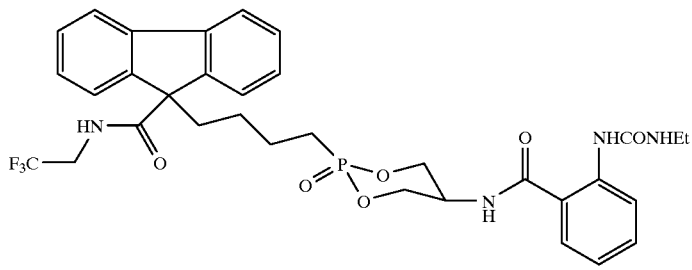
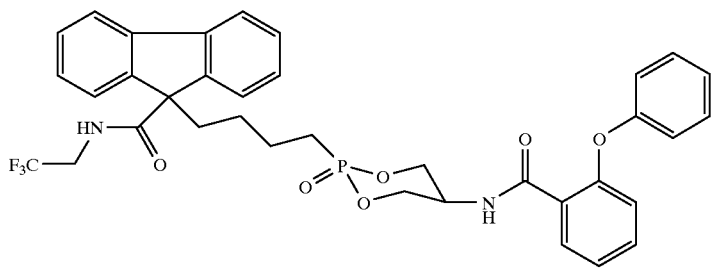
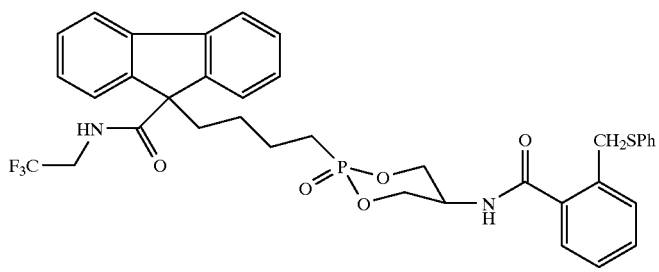

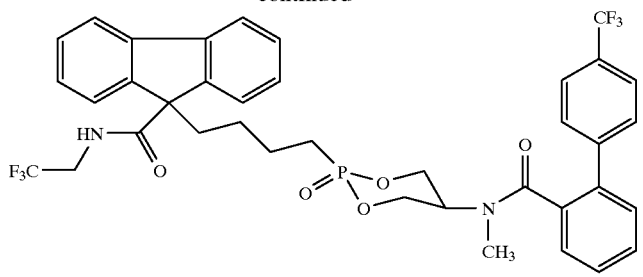
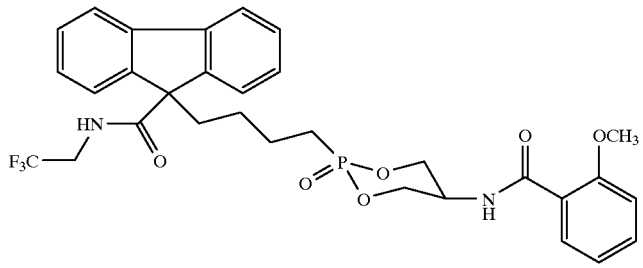
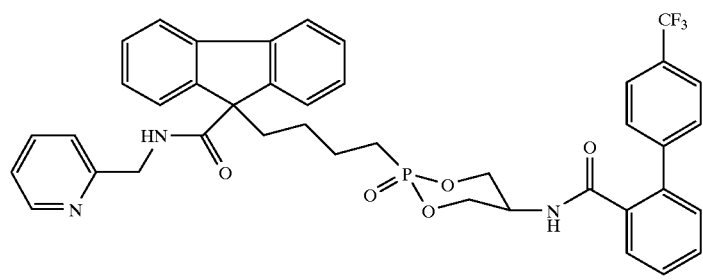
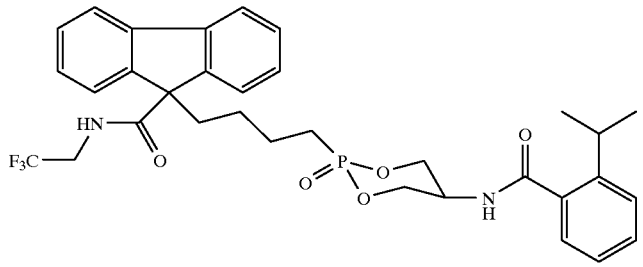
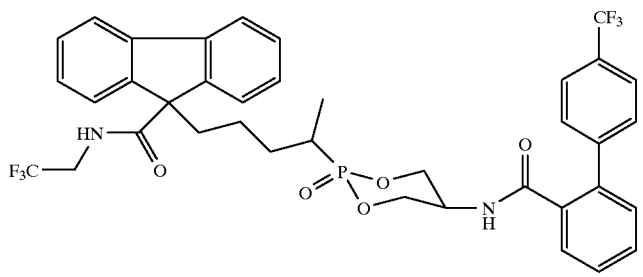
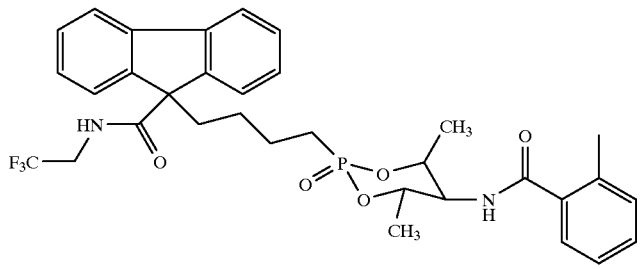

What is claimed is:
1. A compound which has the structure

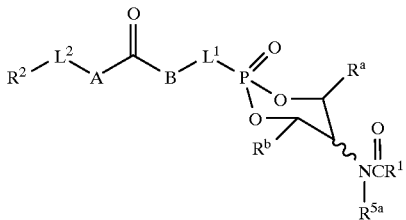

including pharmaceutically acceptable salts thereof, N-oxides thereof,
wherein
A is
(1) a bond;
(2) —O—; or
(3)

where $R^5$ is H or lower alkyl, or $R^5$ together with $R^2$ forms a carbocyclic or heterocyclic ring system containing 4 to 8 members in the ring;

B is a fluorenyl-type group of the structure

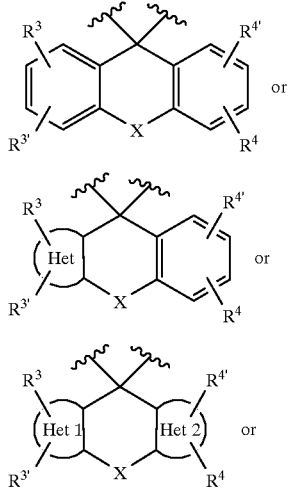

B is an indenyl-type group of the structure

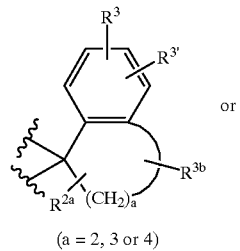

(a = 2, 3 or 4)

-continued

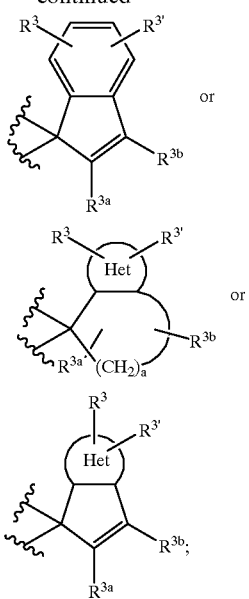

$R^a$ and $R^b$ may be the same or different and are hydrogen, alkyl, aryl, arylalkyl or heteroaryl linked to the ring via a carbon atom;

$R^{5a}$ is H, lower alkyl or aryl;

$R^1$ is independently alkyl, alkenyl, alkynyl, aryl, alkoxy, aryloxy, arylalkoxy, heteroaryl, heteroarylalkoxy, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, halo-alkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl; or $R^1$ and $R^{5a}$ can be joined to form a ring of the structure

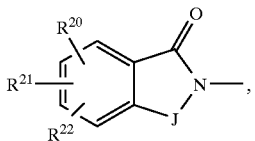

-continued where J is: CHR²³,

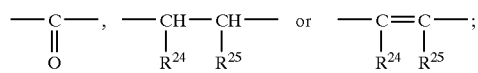

R²³, R²⁴ and R²⁵ are independently hydrogen, alkyl, alkenyl, alkynyl, aryl, arylalkyl, heteroaryl, heteroarylalkyl, cycloalkyl, or cycloalkylalkyl;

R²⁰, R²¹, R²² are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to R¹, or attached via an alkylene at an open position;

R² is hydrogen, alkyl, alkenyl, alkynyl, haloalkyl, alkoxyl, (alkyl or aryl)₃Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, cycloheteroalkyl, cycloheteroalkylalkyl, —PO(R¹³)(R¹⁴), (where R¹³ and R¹⁴ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); cyano, 1,1-(alkoxyl or aryloxy)₂alkyl (where the two aryl or alkyl substituents can be independently defined), R² may be substituted with 1, 2, 3 or 4 substituents, which can be any of substituents for R¹, or haloalkylamino, alkylamino, cycloalkylamino, arylamino, heteroarylamino, alkoxyamino, aryloxyamino, heteroaryloxyamino, heterocyclylamino (where the heterocycle is connected to the carbonyl group via a nitrogen or carbon atom);

L¹ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

L² may be the same or different from L¹ and may independently be any of the L¹ groups set out above or a singe bond;

R³, R³', R⁴ and R⁴' may be the same or different and are independently selected from H, halogen, CF₃, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R³ᵃ and R³ᵇ are the same or different and are independently any of the R³ groups;

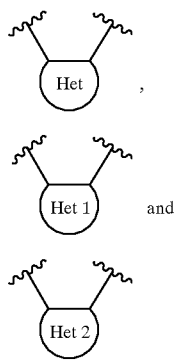

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

(1)

(2)
—O—;

(3)

(4)

(5)

(6)

(7)

wherein
Y is O, N—R⁶ or S;
n' is 0, 1 or 2;
R⁶ is H, lower alkyl, aryl, —C(O)—R¹¹ or —C(O)—O—R¹¹;
R⁷ and R⁸ are the same or different and are independently H, alkyl, aryl, halogen, —O—R¹², or
R⁷ and R⁸ together can be oxygen to form a ketone;
R⁹, R¹⁰, R⁹' and R¹⁰' are the same or different and are independently H, lower alkyl, aryl or —O—R¹¹;
R⁹" and R¹⁰" are the same or different and are independently H, lower alkyl, aryl, halogen or —O—R¹¹;
R¹¹ is alky or aryl;
R¹² is H, alkyl or aryl;
with the proviso that when A is a (1) bond, R²L² cannot be H.

2. The compound as defined in claim 1 wherein A is a bond.

3. The compound as defined in claim 1 wherein A is —O—.

4. The compound as defined in claim 1 wherein A is

5. The compound as defined in claim 1 wherein B is a fluorenyl-type group.
6. The compound as defined in claim 1 wherein B is an indenyl-type group.
7. The compound as defined in claim 1 wherein B is

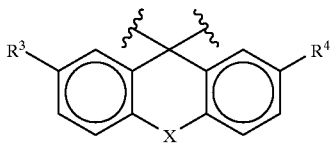

A is NH;
X is a bond, oxygen or sulfur;
$R^3$ and $R^4$ are the same or different and are H or F;
$R^1$ is aryl, phenyl, biphenyl or cycloheteroalkyl;
$R^2$ is aryl, phenyl, heteroaryl, imidazolyl, pyridyl, cyclohexyl, $PO(R^{13})$ $(R^{14})$, heteroarylthio, benzthiazole-2-thio, imidazole-2-thio, alkyl, alkenyl or 1,3-dioxan-2-yl, wherein each of the above is optionally substituted;
$L^1$ is a chain containing 1 to 5 atoms in a linear chain;
$L^2$ is a bond or lower alkylene.

8. The compound as defined in claim 1 which is (E)-9-[4-[2-oxo-5-[[[4'-(trifluoromethyl)[1,1'-biphenyl]-2-yl]carbonyl]amino]-1,3,2-dioxaphosphorinan-2-yl]butyl]-N-(2,2,2-trifluoroethyl)-9H-fluorene-9-carboxamide;

(Z)-9-[4-[2-oxo-5-[[[4'-(trifluoromethyl)-[1,1'-biphenyl]-2-yl]carbonyl]amino]-1,3,2-dioxaphosphorinan-2-yl]butyl]-N-(2,2,2-trifluoroethyl)-9H-fluorene-9-carboxamide;

trans-9-[4-[5-(benzoylamino)-2-oxo-1,3,2-dioxaphosphorinan-2-yl]butyl]-N-(2,2,2-trifluoroethyl)-9H-fluorene-9-carboxamide;

trans-9-[5-[2-oxo-5-[[[4'-(trifluoromethyl)-[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide;

cis-9-[5-[2-oxo-5-[[[4'-(trifluoromethyl)-[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide;

trans-[2-oxo-2-[4-[9-[[(2,2,2-trifluoroethyl)amino]carbonyl]9H-fluoren-9-yl]butyl]-1,3,2-dioxaphosphorinan-5-yl]carbamic acid;

trans-1-(phenylmethyl)-N-[2-[4-[9-[[(2,2,2-trifluoroethyl)amino]carbonyl]-9H-fluoren-9-yl]-butyl]-1,3,2-dioxaphosphorinan-5-yl]-2-piperidinecarboxamide;

trans-9-[4-[2-oxo-5-[[2-(2-pyridinyl)benzoyl]amino]-1,3,2-dioxaphosphorinan-2-yl]butyl]-N-(2,2,2-trifluoroethyl)-9H-fluorene-9-carboxamide;

trans-9-[4-[5-[[2-(2-benzothiazolyl)benzoyl]amino]-2-oxo-1,3,2-dioxaphosphorinan-2-yl]butyl]-N-(2,2,2-trifluoroethyl)-9H-fluorene-9-carboxamide;

trans-9-[4-[5-[[2-(4-morpholinyl)benzoyl]amino]-2-oxo-1,3,2-dioxaphosphorinan-2-yl]butyl]-N-(2,2,2-trifluoroethyl)-9H-fluorene-9-carboxamide;

trans-9-[4-[5-[[2-(2-benzoxazolyl)benzoyl]amino]-2-oxo-1,3,2-dioxaphosphorinan-2-yl]butyl]-N-(2,2,2-trifluoroethyl)-9H-fluorene-9-carboxamide or an ester thereof or an N-oxide thereof, or a pharmaceutically acceptable salt thereof.

9. The compound as defined in claim 1 having the structure

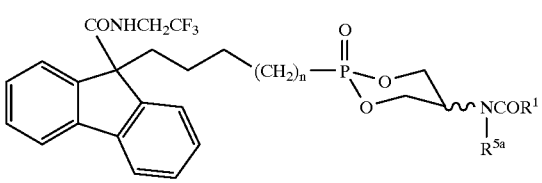

| $R^1CO=$ | n | geometry |
|---|---|---|
| 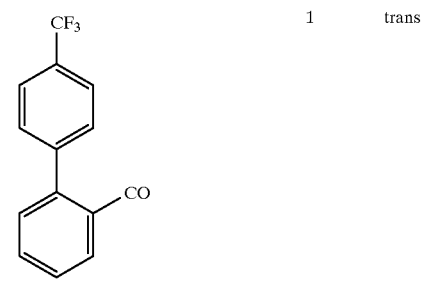 | 1 | trans |
| 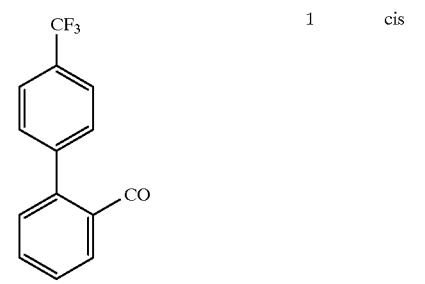 | 1 | cis |
|  | 1 | trans |
| 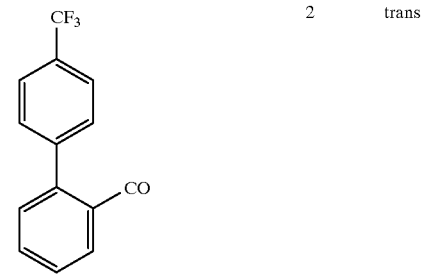 | 2 | trans |

-continued

| R¹CO= | n | geometry |
|---|---|---|
| 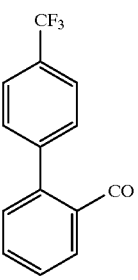 | 2 | cis |
| 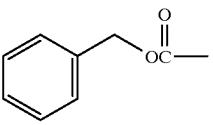 | 1 | trans |
| 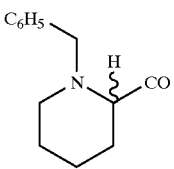 | 1 | trans |
| 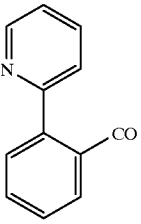 | 1 | trans |
| 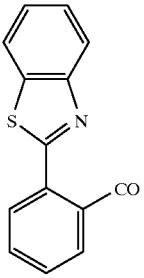 | 1 | trans |
| 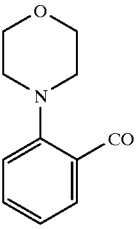 | 1 | trans |

-continued

| R¹CO= | n | geometry |
|---|---|---|
| 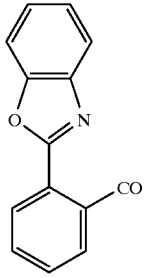 | 1 | trans |

10. The compound as defined in claim 1 having the name (E)-9-[4-[2-oxo-5-[[[4'-(trifluoromethyl)-[1,1'-biphenyl]-2-yl]carbonyl]amino]-1,3,2-dioxa-phosphorinan-2-yl]butyl]-N-(2,2,2-trifluoroethyl)-9H-fluorene-9-carboxamide;

trans-9-[4-[5-(benzoylamino)-2-oxo-1,3,2-dioxaphosphorinan-2-yl]butyl]-N-(2,2,2-trifluoroethyl)-9H-fluorene-9-carboxamide;

trans-9-[5-[2-oxo-5-[[[4'-(trifluoromethyl)-[1,1'-biphenyl]-2-yl]carbonyl]amino]-1,3,2-dioxaphosphorinan-2-yl]pentyl]-N-(2,2,2-trifluoroethyl)-9H-fluorene-9-carboxamide;

trans-[2-oxo-2-[4-[9-[[(2,2,2-trifluoroethyl)amino]carbonyl]9H-fluoren-9-yl]butyl]-1,3,2-dioxaphosphorinan-5-yl]carbamic acid;

trans-1-(phenylmethyl)-N-[2-[4-[9-[[(2,2,2-trifluoroethyl)amino]carbonyl]-9H-fluoren-9-yl]butyl]-1,3,2-dioxaphosphorinan-5-yl]-2-piperidinecarboxamide;

trans-9-[4-[2-oxo-5-[[2-(2-pyridinyl)benzoyl]amino]-1,3,2-dioxaphosphorinan-2-yl]butyl]-N-(2,2,2-trifluoroethyl)-9H-fluorene-9-carboxamide;

trans-9-[4-[5-[[2-(2-benzothiazolyl)benzoyl]amino]-2-oxo-1,3,2-dioxaphosphorinan-2-yl]butyl]-N-(2,2,2-trifluoroethyl)-9H-fluorene-9-carboxamide;

trans-9-[4-[5-[[2-(4-morpholinyl)benzoyl]amino]-2-oxo-1,3,2-dioxaphosphorinan-2-yl]butyl]-N-(2,2,2-trifluoroethyl)-9H-fluorene-9-carboxamide;

trans-9-[4-[5-[[2-(2-benzoxazolyl)benzoyl]amino]-2-oxo-1,3,2-dioxaphosphorinan-2-yl]butyl]-N-(2,2,2-trifluoroethyl)-9H-fluorene-9-carboxamide; or an N-oxide thereof, or pharmaceutically acceptable salts thereof or esters thereof.

11. The compound as defined in claim 1 wherein A is NH and $R^2L^2$ is $CF_3CH_2$.

12. A method for preventing, inhibiting or treating atherosclerosis, pancreatitis, hyperglycemia or obesity in a mammalian species, which comprises administering to a patient in need of treatment a therapeutically effective amount of a compound as defined in claim 1.

13. A method of lowering serum lipid levels, cholesterol and/or triglycerides, or inhibiting and/or treating hyperlipemia, hyperlipidemia, hyperlipoproteinemia, hypercholesterolemia and/or hypertriglyceridemia, and/or preventing, inhibiting or treating atherosclerosis, pancreatitis or obesity in a mammalian species, which comprises administering to a patient in need of treatment a therapeutically effective amount of a compound as defined in claim 1.

14. The method as defined in claim 13 where B is

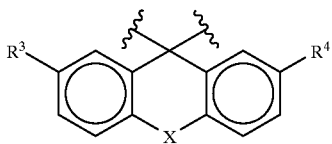

A is NH;

X is a bond, oxygen or sulfur;

$R^3$ and $R^4$ are the same or different and are H or F;

$R^1$ is aryl, phenyl, biphenyl or cycloheteroalkyl;

$R^2$ is aryl, phenyl, heteroaryl, imidazolyl, pyridyl, cyclohexyl, $PO(R^{13})(R^{14})$, heteroarylthio, benzthiazole-2-thio, imidazole-2-thio, alkyl or alkenyl, 1,3-dioxan-2-yl, wherein each of the above is optionally substituted;

$L^1$ is a chain containing 1 to 5 atoms in a linear chain;

$L^2$ is a bond or lower alkylene.

15. The method as defined in claim 12 where B is

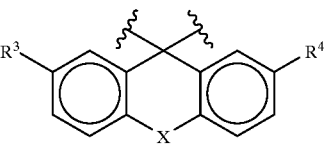

X is a bond, oxygen or sulfur;

$R^3$ and $R^4$ are the same or different and are H or F;

$R^2$ is aryl, phenyl, heteroaryl, imidazolyl, pyridyl, cyclohexyl, $PO(R^{13})(R^{14})$, heteroarylthio, benzthiazole-2-thio, imidazole-2-thio, alkyl or alkenyl, 1,3-dioxan-2-yl, wherein each of the above is optionally substituted;

$R^1$ is phenyl, biphenyl or piperidine;

$L^1$ is a chain containing 1 to 5 atoms in a linear chain;

$L^2$ is a bond or lower alkylene.

* * * * *